(12) United States Patent
Goodnow

(10) Patent No.: US 6,790,661 B1
(45) Date of Patent: Sep. 14, 2004

(54) SYSTEM FOR DETECTING BACTERIA IN BLOOD, BLOOD PRODUCTS, AND FLUIDS OF TISSUES

(75) Inventor: Timothy T. Goodnow, North Andover, MA (US)

(73) Assignee: Verax Biomedical, Inc., Woburn, MA (US)

( * ) Notice: Subject to any disclaimer, the term of this patent is extended or adjusted under 35 U.S.C. 154(b) by 0 days.

(21) Appl. No.: 09/616,283

(22) Filed: Jul. 14, 2000

Related U.S. Application Data

(60) Provisional application No. 60/144,442, filed on Jul. 16, 1999.

(51) Int. Cl.[7] .................. A61K 51/00; A61K 49/00; A61B 5/055; A01N 63/00; A01N 65/00
(52) U.S. Cl. .................. 435/332; 424/1.49; 424/9.2; 424/9.34; 424/93.1; 424/93.48; 424/137.1; 424/150.1; 424/163.1; 424/164.1; 424/165.1; 424/169.1; 424/178.1; 424/184.1; 424/278.1; 435/2; 435/7.1; 435/7.32; 435/7.37; 435/7.92; 435/7.93; 435/7.94; 435/7.95; 435/69.6; 435/174; 435/176; 435/177; 435/325; 436/20; 436/21
(58) Field of Search .................. 424/1.49, 9.34, 424/93.1–93.48, 137.1, 150.1, 164.1, 165.1–169.1; 435/2, 7.1, 7.32–7.37, 7.92–7.95, 174, 176, 177, 340

(56) References Cited

U.S. PATENT DOCUMENTS

| | | | |
|---|---|---|---|
| 4,497,899 A | 2/1985 | Armstrong et al. | 436/510 |
| 4,618,576 A | 10/1986 | Rosenstein et al. | 435/7 |

(List continued on next page.)

FOREIGN PATENT DOCUMENTS

| | | |
|---|---|---|
| EP | 0183876 A1 | 6/1986 |
| EP | 0217527 B1 | 4/1987 |
| EP | 0271379 A1 | 6/1988 |

(List continued on next page.)

OTHER PUBLICATIONS

Erich et al. 1989. J. of Immuno. vol. 143 (12): 4053–4060.*
Tadler et al. J. of Clin. Lab. Anal. 3:21–25 (1989).*

(List continued on next page.)

Primary Examiner—Lynette R. F. Smith
Assistant Examiner—J. Hines
(74) Attorney, Agent, or Firm—Ropes & Gray LLP

(57) ABSTRACT

The invention provides methods for screening for the presence of a clinically relevant amount of bacteria in donor blood or a blood product from a donor mammal, particularly blood or a blood product that will be transferred from the donor mammal to a recipient mammal. The method comprises contacting a sample of the donor blood or a blood product with a set of binding agents that comprises binding agents that specifically bind to Gram-negative bacterial antigen and/or binding agents that specifically bind to Gram-positive bacterial antigen, and determining binding of the set of binding agents to the sample, wherein binding indicates the presence of a clinically relevant amount of Gram-positive bacteria and/or Gram-negative bacteria in the donor blood or blood product and no binding indicates the absence of a clinically relevant amount of Gram-positive bacteria and/or Gram-negative bacteria in the donor blood or blood product.

The invention further provides methods and kits for screening for the presence of a clinically relevant amount of Gram-positive bacteria, Gram-negative bacteria, or both Gram-positive and Gram-negative bacteria in a donor tissue by screening the fluid in which the donor tissue is stored.

20 Claims, 6 Drawing Sheets

U.S. PATENT DOCUMENTS

| | | | | |
|---|---|---|---|---|
| 4,683,196 A | * | 7/1987 | McLaughlin | 435/7 |
| 4,831,126 A | | 5/1989 | Bundle et al. | 536/53 |
| 4,847,199 A | | 7/1989 | Snyder et al. | 435/36 |
| 4,918,163 A | | 4/1990 | Young et al. | 530/387 |
| 5,043,267 A | * | 8/1991 | Richards | 435/7.31 |
| 5,057,598 A | | 10/1991 | Pollack et al. | 530/387 |
| 5,093,235 A | | 3/1992 | Williams et al. | 435/7.32 |
| 5,096,837 A | | 3/1992 | Fan et al. | 436/514 |
| 5,139,933 A | | 8/1992 | Green et al. | 435/732 |
| 5,179,018 A | | 1/1993 | Bogard, Jr. et al. | 530/388.15 |
| 5,200,323 A | * | 4/1993 | Chan et al. | 435/18 |
| 5,322,788 A | | 6/1994 | Drouin | 435/240.27 |
| 5,356,778 A | | 10/1994 | Hansen et al. | 435/7.2 |
| 5,426,046 A | | 6/1995 | Kaplan et al. | 435/240.27 |
| 5,491,068 A | | 2/1996 | Benjamin et al. | 435/7.32 |
| 5,523,288 A | | 6/1996 | Cohen et al. | 514/12 |
| 5,610,075 A | | 3/1997 | Stahl-Rees | 436/501 |
| 5,635,348 A | | 6/1997 | Leong | 435/6 |
| 5,695,946 A | | 12/1997 | Benjamin et al. | 435/7.32 |
| 5,698,198 A | * | 12/1997 | Young | 424/150.1 |
| 5,747,277 A | | 5/1998 | Tsuchiya | 435/34 |
| 5,750,357 A | | 5/1998 | Olstein et al. | 435/7.32 |
| 5,773,234 A | | 6/1998 | Pronovost et al. | 435/7.36 |
| 5,773,306 A | | 6/1998 | Neely | 436/518 |
| H1775 H | | 1/1999 | Ligler et al. | 435/7.32 |
| 5,858,728 A | | 1/1999 | Gram et al. | 435/70.21 |
| 5,869,272 A | | 2/1999 | Bogart et al. | 435/7.32 |
| 5,888,754 A | | 3/1999 | Pandian et al. | 435/7.92 |
| 5,888,760 A | | 3/1999 | Godsey et al. | 435/34 |

FOREIGN PATENT DOCUMENTS

| | | | | |
|---|---|---|---|---|
| EP | 0279517 | | 8/1988 | |
| EP | 0286099 A2 | | 10/1988 | |
| EP | 0224830 B1 | | 1/1991 | |
| EP | 0074240 B1 | | 3/1991 | |
| EP | 0163493 B1 | | 3/1991 | |
| EP | 462462 | * | 5/1991 | G01N/33/543 |
| EP | 0151128 B1 | | 7/1991 | |
| EP | 0174204 B1 | | 11/1991 | |
| EP | 0279517 B1 | | 11/1991 | |
| EP | 279517 | * | 11/1991 | G01N/33/53 |
| EP | 0481970 A3 | | 4/1992 | |
| EP | 0494085 A1 | | 7/1992 | |
| EP | 0265672 B1 | | 3/1993 | |
| EP | 0160670 B1 | | 5/1993 | |
| EP | 0539497 B1 | | 6/1995 | |
| EP | 0496409 B1 | | 10/1996 | |
| EP | 0763737 A1 | | 3/1997 | |
| WO | WO 85/02685 | | 6/1985 | |
| WO | WO 90/03186 | | 4/1990 | |
| WO | WO 90/11370 | | 10/1990 | |
| WO | 96/40251 | | 12/1996 | |
| WO | WO 98/57994 | * | 12/1998 | C07K/16/00 |

OTHER PUBLICATIONS

Arduino et al. 1989. J. of Clin. Microbio. 27(7): 1483–1485.*

Tadler et al. 1989. J. of Clin. Lab. Ana. 3:21–25.*

Arduino, Matthew J., et al., "Growth and Endotoxin Production of *Yersinia enterocolitica* and *Enterobacter agglomerans* in Packed Erythrocytes," *Journal of Clinical Microbiology* vol. 27, No. 7: 1483–1485 (1989).

Brecher, M.E., et al., "Vancomycin Linked Probes and Microvolume Fluorimetry For the Rapid Detection of Gram Positive Bacterial Contamination in Platelet Products," *Transfusion* vol. 38, Supplement: 106S Abstract # S402 (1998).

Brecher, M.E., "Platelet Bacterial Contamination and the Use of a Chemiluminescence–Linked Universal Bacterial Ribosomal RNA Gene Probe," *Transfusion* vol. 34, No. 9: 750–755 (1994).

Feng, P. et al., "Direct Identification of *Yersinia enterocolitica* in Blood by Polymerase Chain Reaction Amplification," *Transfusion* vol. 32, No. 9: 850–854 (1992).

Kim, D.M. et al., "Prestorage Removal of *Yersinia enterocolitica* From Red Cells with White Cell–Reduction Filters," *Transfusion* vol. 32, No. 7: 658–662 (1992).

Klein, H.G. et al., "Current Status of Microbial Contamination of Blood Components: Summary of a Conference," *Transfusion* vol. 37: 95–101 (1997).

Mitchell, Karen–Mae T. and Mark E. Brecher, "Approaches to the Detection of Bacterial Contamination in Cellular Blood Products," *Transfusion Medicine Reviews* vol. 13, No. 2: 132–144 (1999).

Novitsky, Thomas J., "LAL: Discovery and Commercial Development," *LAL Update* vol. 14, No. 2: 1–4 (1996).

Pyrochrome® Product Insert, Manufactured by Associates of Cape Cod, Inc.

Tadler, Monica B. et al., "Sandwich Immunoassay for the Detection of Lipoteichoic Acid," *Journal of Clinical Laboratory Analysis* vol. 3: 21–25 (1989).

Wagner, Stephen J., "The Potential for Bacterial Testing of Blood Products," *Zbl. Bakt. vol. 283:* 253–257 (1996).

* cited by examiner

Colored Latex   Anti Bacteria-
Anti Bacteria

Bacteria   Colored Latex   Anti Bacteria
Anti Bacteria

1st Binding   Anti Bacteria
Reaction

Colored Spot
Visible

2nd Binding
Reaction

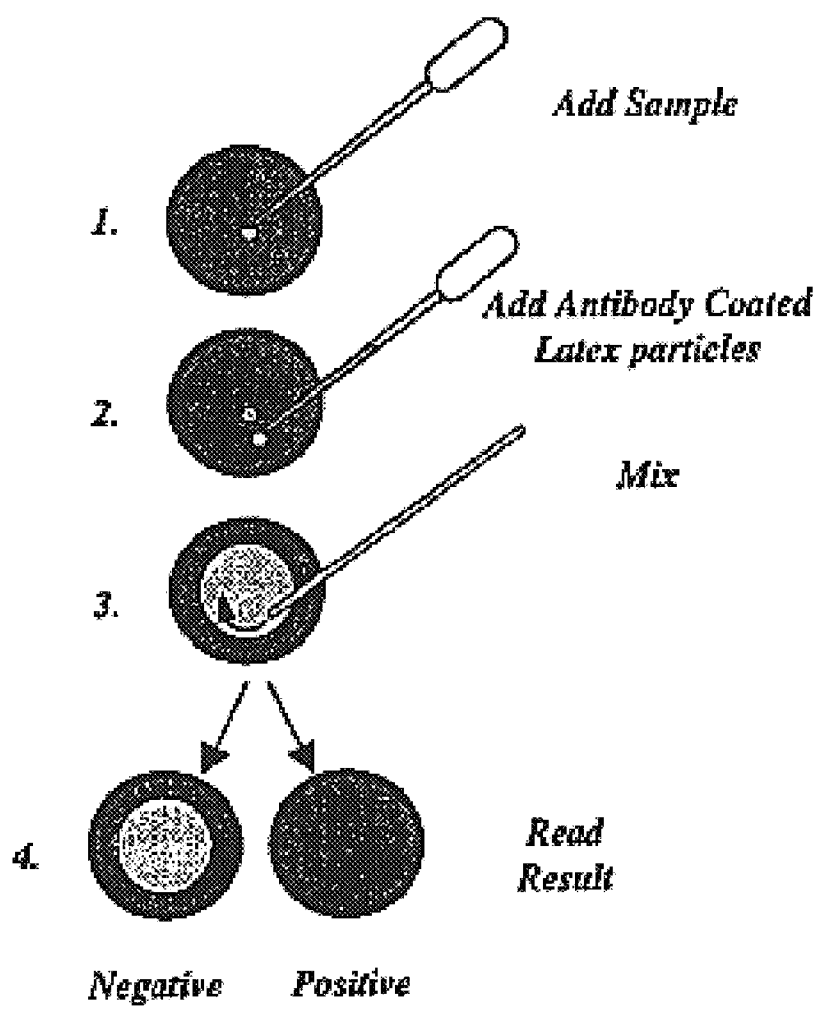

SYSTEM FOR DETECTING BACTERIA IN BLOOD, BLOOD PRODUCTS, AND FLUIDS OF TISSUES

CROSS-REFERENCE TO RELATED APPLICATIONS

This application claims benefit from U.S. Provisional Patent Application No. 60/144,442 filed Jul. 16, 1999, the entire contents of which is hereby incorporated by reference.

BACKGROUND OF THE INVENTION

1. Field of the Invention

The invention relates to the screening of blood or a blood product (including whole blood, hematopoietic stem cells, leukocytes, plasma, serum, red blood cells, and platelets) or a donor tissue for the presence of a clinically relevant amount of bacteria More particularly, the invention relates to the screening for the presence of a clinically relevant amount of contaminating bacteria in blood and blood products or donor tissue that will be used for transfusion or transplantation.

2. Summary of the Related Art

Transfusion of blood and blood products is a therapeutically important aspect of patient care. Transplantation of donor tissues and organs is likewise therapeutically important. The absence of clinically relevant levels of contaminating bacteria in donor blood, donor blood product, or a donor tissue or organ is a requirement necessary for the safe, therapeutic use of these donated fluids and tissues for transfusion or transplantation. For example, bacteremia (the invasion of bacteria into the blood) can be transient, continuous, or intermittent. Wagner et al. (Clin. Microbiol. Rev. 7: 290–302 (1994)) and Goldman et al. (Trans. Med. Revs. 5: 73–83 (1991)) teach that a large number of different species of bacteria have been identified in contaminated blood transfused to patients who, following transfusion, developed septicimia. Tadler et al. (J. Clin. Laboratory Analysis 2: 21–25 (1989)) teaches that although transient bacteremia is generally of little consequence, continuous or intermittent bacteremia can present life-threatening situations for several patient populations, particularly immunocompromised, neonatal, and geriatric patients. Thus, if blood contaminated with a clinically relevant amount of bacteria were to be transfused to a recipient patient, the recipient patient might suffer complications, particularly since transfusions of blood and/or blood products are often performed when the patient is undergoing major surgery, or is otherwise vulnerable.

Similarly, donor tissues and organs are preferably microbe-free to retard and, preferably, prevent rejection by the recipient.

Despite the need for a safe, microbe-free supply of blood or a blood product, no rapid, efficient method exists for detecting the presence of contaminating bacteria in blood or a blood product. Although there are methods for determining whether or not blood is infected with bacteria, most current bacterial testing is done on patients suspected of having infected blood, with the prime intent of identifying the exact micro-organism that is causing the infection, so that the appropriate antibiotic therapy can begin. In these methods, to identify the infecting bacteria, a sample of patient blood is grown in a culture media that favors the growth of the bacteria for a relatively long period of time. Eventually, the number of micro-organisms present is amplified to the point that a reasonable quantity exists and can be detected.

Although these culture-based blood testing techniques are useful for determining the particular type of bacteria that is infecting a patient's blood, the length of the time required to perform these techniques makes them impractical to use to test donor blood and blood products or donor organs. This is because donor blood, blood products, and organs are often needed for use as transfusions or transplantations on relatively short notice. Thus, there may be no time to test the donated blood (or blood product) or organ with a culture-based technique before the donated blood or organ is needed for use.

In addition, donated organs and blood or blood products have a relatively short shelf-life due not only to a loss of function of the donated material, but also to an increase in amount of any contaminating bacteria present. Since bacteria have a rapid propagation rate, even a small amount of contaminating bacteria present in the donated blood or blood product will quickly amplify with time. For example, while donated platelets are functionally viable only 7 days post-donation, they are rarely used more than 5 days post-donation for fear of bacterial contamination that, when donated, may not have been significant but, over time, may have increased to a level that is clinically relevant. Moreover, these culture-based blood testing techniques take too long to routinely screen platelets, which have a short shelf-life (approximately 5 days post-donation), for transfusion use.

Brecher et al. (Transfusion 34(9): 750–755 (1994)) teaches another technique for detecting a particular contaminating bacteria in blood using labelled nucleic acid probes to hybridize to the genetic material of potential contaminants The probes used in these studies, however, are very limited in the number of micro-organisms that can be detected and, unfortunately, no commercially viable test has emerged from this technology. Given their complexity, these techniques are too labor-intensive and too time-costly to be routinely used to screen blood or blood products for bacterial contamination.

There is, therefore, a need for a technique for rapidly detecting the presence of a clinically relevant amount of any contaminating bacteria in donor blood or a blood product, or in a donor tissue. Ideally, antigen binding techniques could be rapidly and effectively employed. Unfortunately, Wagner, S. J. (Int. J. Med. Microbiol. Virol. Parasitol. Infect. Dis. 283(3):253–257 (1996)) teaches that no common antigenic source exists for broad based bacterial detection. Thus, there is a need for antigen binding-based techniques for detecting clinically relevant amounts of contaminating bacteria in donor blood or blood products or in donor tissues.

BRIEF SUMMARY OF THE INVENTION

The invention provides rapid antigen binding-based methods for detecting clinically relevant amounts of contaminating bacteria in blood or blood products or in donor tissue, particularly donor blood or blood products or donor tissue to be transferred from one individual to another.

Accordingly, in a first aspect, the invention provides a method for screening for the presence of a clinically relevant amount of bacteria in donor blood or a donor blood product from a donor mammal for transfer to a recipient mammal comprising contacting a sample of blood or a blood product with a set of binding agents, wherein the set of binding agents comprises binding agents that specifically bind to a Gram-negative bacterial antigen and binding agents that specifically bind to a Gram-positive bacterial antigen, and determining binding of the set of binding agents to the sample, wherein binding indicates the presence of a clinically relevant amount of bacteria in the donor blood or blood product and no binding indicates the absence of a clinically relevant amount of bacteria in the donor blood or blood product.

In certain embodiments of the first aspect of the invention, the sample is treated prior to or concomitantly with contacting the sample with the set of binding agents. Preferably, the treatment exposes a binding site of the binding agent on the Gram-negative bacterial antigen or on the Gram-positive bacterial antigen. In certain embodiments of the first aspect of the invention, the donor blood or blood product determined to have an absence of a clinically relevant amount of bacteria is administered to a recipient mammal. Preferably, the donor mammal and the recipient mammal are of the same species. In certain preferred embodiments, the binding agents that specifically bind to a Gram-negative bacterial antigen comprise antibodies or antibody derivatives that specifically bind to a Gram-negative bacterial antigen. In certain preferred embodiments, the binding agents that specifically bind to a Gram-negative bacterial antigen thereof comprise a molecule selected from the group consisting of a Limulus anti-lipopolysaccharide factor (LALF), a lipopolysaccharide binding protein (LBP), a bactericidal/permeability-increasing protein (BPI), and an antibiotic, such as polymixin or bacitracin. Preferably, the binding agents that specifically bind to a Gram-negative bacterial antigen specifically bind to the lipopolysaccharide structure of the Gram-negative bacteria. In certain preferred embodiments, the binding agents that specifically bind to a Gram-positive bacteria antigen comprise antibodies or antibody derivatives that specifically bind to a Gram-positive bacterial antigen. In certain embodiments, the binding agents that specifically bind to a Gram-positive bacterial antigen comprise an antibiotic, wherein the antibiotic is not vancomycin. Preferably, the binding agents that specifically bind to a Gram-positive bacterial antigen specifically bind to the lipotechoic acid structure of the Gram-positive bacteria.

In various embodiments of the first aspect of the invention, the binding agents that specifically bind to a Gram-negative bacterial antigen are detectably labeled with a first reporter molecule and the binding agents that specifically bind to a Gram-positive bacterial antigen are detectably labeled with a second reporter molecule. In certain embodiments, the first reporter molecule and the second reporter molecule are the same. In another embodiment, the first reporter molecule and the second reporter molecule are not the same. Preferably, one or both of the first reporter molecule and the second reporter molecule is a molecule with enzymatic activity, a radio-labeled molecule, a fusion molecule, a fluorogenic molecule, a metal sol, a particle, a chromatic molecule, or a molecule that is specifically bound by a secondary binding agent.

In a second aspect, the invention provides method for screening for the presence of a clinically relevant amount of Gram-positive bacteria in donor blood or a blood product from a donor mammal for transfer to a recipient mammal comprising contacting a sample of the donor blood or a blood product with a set of binding agents, wherein the set of binding agents comprises binding agents that specifically bind to Gram-positive bacterial antigen, and determining binding of the set of binding agents to the sample, wherein binding indicates the presence of a clinically relevant amount of Gram-positive bacteria in the donor blood or blood product and no binding indicates the absence of a clinically relevant amount of Gram-positive bacteria in the donor blood or blood product.

In certain embodiments of the second aspect of the invention, the sample is treated prior to or concomitantly with contacting the sample with the set of binding agents. Preferably, the treatment exposes a binding site for the binding agent on the Gram-positive bacterial antigen. In certain embodiments, the blood or blood product determined to have an absence of a clinically relevant amount of Gram-positive bacteria is transferred to a recipient mammal. Preferably, the donor mammal and the recipient mammal are of the same species. In certain preferred embodiments, the binding agents that specifically bind to a Gram-positive bacterial antigen comprise antibodies or antibody derivatives that specifically bind to a Gram-positive bacterial antigen. In certain embodiments, the binding agents that specifically bind to a Gram-positive bacterial antigen comprise an antibiotic, wherein the antibiotic is not vancomycin. Preferably, the binding agents that specifically bind to a Gram-positive bacterial antigen specifically bind to the lipotechoic acid structure of the Gram-positive bacteria.

In various embodiments of the second aspect of the invention, the binding agents that specifically bind to a Gram-positive bacterial antigen are detectably labeled with a reporter molecule. Preferably, the reporter molecule is a molecule with enzymatic activity, a radio-labeled molecule, a fusion molecule, a fluorogenic molecule, a metal sol a particle, a chromatic molecule, or a molecule that is specifically bound by a secondary binding agent.

In a third aspect, the invention provides a method for screening for the presence of a clinically relevant amount of Gram-negative bacteria in donor blood or a blood product from a donor mammal for transfer to a recipient mammal comprising contacting a sample of blood or a blood product with a set of binding agents, wherein the set of binding agents comprises binding agents that specifically bind to Gram-negative bacterial antigen, and determining binding of the set of binding agents to the sample, wherein binding indicates the presence of a clinically relevant amount of Gram-negative bacteria in the donor blood or blood product and no binding indicates the absence of a clinically relevant amount of Gram-negative bacteria in the donor blood or blood product.

In certain embodiments of the third aspect of the invention, the sample is treated prior to or concomitantly with contacting the sample with the set of binding agents. Preferably, the treatment exposes a binding site for the binding agent on the Gram-negative bacterial antigen. In certain embodiments, the donor blood or blood product determined to have an absence of a clinically relevant amount of Gram-negative bacteria is transferred to a recipient mammal. Preferably, the donor mammal and the recipient mammal are of the same species. In certain preferred embodiments, the binding agents that specifically bind to a Gram-negative bacterial antigen comprise antibodies or antibody derivatives that specifically bind to a Gram-negative bacterial antigen. In certain preferred embodiments, the binding agents that specifically bind to a Gram-negative bacterial antigen comprise a molecule selected from the group consisting of a Limulus anti-lipopolysaccharide factor (LALF), a lipopolysaccharide binding protein (LBP), a bactericidal/permeability-increasing protein (BPI), and an antibiotic, such as polymixin or bacitracin. Preferably, the binding agents that specifically bind to a Gram-negative bacterial antigen specifically bind to the lipopolysaccharide structure of the Gram-negative bacteria.

In various embodiments of the third aspect of the invention, the binding agents that specifically bind to a Gram-negative bacterial antigen are detectably labeled with a reporter molecule. Preferably, the reporter molecule is a molecule with enzymatic activity, a radio-labeled molecule, a fusion molecule, a fluorogenic molecule, a metal sol, a particle, a chromatic molecule, or a molecule that is specifically bound by a secondary binding agent.

In a fourth aspect, the invention provides a kit for screening for the presence of a clinically relevant amount of bacteria in donor blood or a donor blood product from a donor mammal for transfer to a recipient mammal comprising a set of binding agents, wherein the set of binding agents comprises binding agents that specifically bind to Gram-negative bacterial antigen and binding agents that specifically bind to Gram-positive bacterial antigen, and a means for detecting binding of the set of binding agents to a sample of the donor blood or blood product, wherein binding indicates the presence of a clinically relevant amount of bacteria in the donor blood or blood product and no binding indicates the absence of a clinically relevant amount of bacteria in the donor blood or blood product.

In certain embodiments of the fourth aspect of the invention, the kit further comprises a means for treating the sample, wherein the treatment exposes a binding site for the binding agent on the Gram-negative bacterial antigen or on the Gram-positive bacterial antigen. In certain embodiments of the fourth aspect of the invention, the donor blood or blood product determined to have an absence of a clinically relevant amount of bacteria is transferred to a recipient mammal. Preferably, the donor mammal and the second mammal are of the same species. In certain preferred embodiments, the binding agents that specifically bind to a Gram-negative bacterial antigen comprise antibodies or antibody derivatives that specifically bind to a Gram-negative bacterial antigen. In certain preferred embodiments, the binding agents that specifically bind to a Gram-negative bacterial antigen comprise a molecule selected from the group consisting of a Limulus anti-lipopolysaccharide factor (LALF), a lipopolysaccharide binding protein (LBP), a bactericidal/permeability-increasing protein (BPI), and an antibiotic, such as polymixin or bacitracin. Preferably, the binding agents that specifically bind to a Gram-negative bacterial antigen specifically bind to the lipopolysaccharide structure of the Gram-negative bacteria. In certain preferred embodiments, the binding agents that specifically bind to a Gram-positive bacterial antigen comprise antibodies or antibody derivatives that specifically bind to a Gram-positive bacterial antigen. In certain embodiments, the binding agents that specifically bind to a Gram-positive bacterial antigen comprise an antibiotic, wherein the antibiotic is not vancomycin. Preferably, the binding agents that specifically bind to a Gram-positive bacterial antigen specifically bind to the lipotechoic acid structure of the Gram-positive bacteria.

In various embodiments of the fourth aspect of the invention, the binding agents that specifically bind to a Gram-negative bacterial antigen are detectably labeled with a first reporter molecule and the binding agents that specifically bind to a Gram-positive bacterial antigen are detectably labeled with a second reporter molecule. In certain embodiments, the first reporter molecule and the second reporter molecule are the same. In another embodiment, the first reporter molecule and the second reporter molecule are not the same. Preferably, one or both of the first reporter molecule and the second reporter molecule is a molecule with enzymatic activity, a radio-labeled molecule, a fusion molecule, a fluorogenic molecule, a metal sol, a particle, a chromatic molecule, or a molecule that is specifically bound by a secondary binding agent.

In a fifth aspect, the invention provides a kit for screening for the presence of a clinically relevant amount of Gram-positive bacteria in donor blood or a donor blood product from a donor mammal for transfer to a recipient mammal comprising a set of binding agents, wherein the set of binding agents comprises binding agents that specifically bind to a Gram-positive bacterial antigen, and a means for detecting binding of the set of binding agents to a sample of the blood or blood product, wherein binding indicates the presence of a clinically relevant amount of Gram-positive bacteria in the donor blood or blood product and no binding indicates the absence of a clinically relevant amount of Gram-positive bacteria in the donor blood or blood product.

In certain embodiments of the fifth aspect of the invention, the kit further comprises a means for treating the sample, wherein the treatment exposes a binding site for the binding agent on the Gram-positive bacterial antigen. In certain embodiments, the donor blood or blood product determined to have an absence of a clinically relevant amount of bacteria is transferred to a recipient mammal. Preferably, the donor mammal and the recipient mammal are of the same species. In certain preferred embodiments, the binding agents that specifically bind to a Gram-positive bacterial antigen comprise antibodies or antibody derivatives that specifically bind to a Gram-positive bacterial antigen. In certain embodiments, the binding agents that specifically bind to a Gram-positive bacterial antigen comprise an antibiotic, wherein the antibiotic is not vancomycin. Preferably, the binding agents that specifically bind to a Gram-positive bacterial antigen specifically bind to the lipotechoic acid structure of the Gram-positive bacteria.

In various embodiments of the fifth aspect of the invention, the binding agents that specifically bind to a Gram-positive bacterial antigen are detectably labeled with a reporter molecule. Preferably, the reporter molecule is a molecule with enzymatic activity, a radio-labeled molecule, a fusion molecule, a fluorogenic molecule, a metal sol, a particle, a chromatic molecule, or a molecule that is specifically bound by a secondary binding agent.

In a sixth aspect, the invention provides a kit for screening for the presence of a clinically relevant amount of Gram-negative bacteria in donor blood or a donor blood product from a donor mammal for transfer to a recipient mammal comprising a set of binding agents, wherein the set of binding agents comprises binding agents that specifically bind to a Gram-negative bacterial antigen, and a means for detecting binding of the set of binding agents to a sample of the blood or blood product, wherein binding indicates the presence of a clinically relevant amount of Gram-negative bacteria in the donor blood or blood product and no binding indicates the absence of a clinically relevant amount of Gram-negative bacteria in the donor blood or blood product.

In certain embodiments of the sixth aspect of the invention, the kit further comprises a means for treating the sample, wherein the treatment exposes a binding site for the binding agent on the Gram-negative bacterial antigen. In certain embodiments, the donor blood or blood product determined to have an absence of a clinically relevant amount of Gram-negative bacteria is transferred to a recipient mammal. Preferably, the donor mammal and the recipient mammal are of the same species. In certain preferred embodiments, the binding agents that specifically bind to a Gram-negative bacterial antigen comprise antibodies or antibody derivatives that specifically bind to a Gram-negative bacterial antigen. In certain preferred embodiments, the binding agents that specifically bind to a Gram-negative bacterial antigen comprise a molecule selected from the group consisting of a Limulus anti-lipopolysaccharide factor (LALF), a lipopolysaccharide binding protein (LBP), a bactericidal/permeability-increasing protein (BPI), and an antibiotic, such as polymixin or bacitracin. Preferably, the binding agents that specifically bind to a Gram-negative bacterial antigen specifically bind to the lipopolysaccharide structure of the Gram-negative bacteria.

In various embodiments of the sixth aspect of the invention, the binding agents that specifically bind to a Gram-negative bacterial antigen are detectably labeled with a reporter molecule. Preferably, the reporter molecule is a molecule with enzymatic activity, a radio-labeled molecule, a fusion molecule, a fluorogenic molecule, a metal sol, a particle, a chromatic molecule, or a molecule that is specifically bound by a secondary binding agent.

In various embodiments of the first, second, third, fourth, fifth, and sixth aspect of the invention, the blood or blood product is preferably whole blood, leukocytes, hematopoietic stem cells, platelets, red blood cells, plasma, or serum.

In a seventh aspect, the invention provides a method for screening for the presence of a clinically relevant amount of bacteria in a tissue from a mammal wherein the tissue is stored in a fluid, comprising contacting a sample of the fluid with a set of binding agents, wherein the set of binding agents comprises binding agents that specifically bind to a Gram-negative bacterial antigen and binding agents that specifically bind to a Gram-positive bacterial antigen, and determining binding of the set of binding agents to the sample, wherein binding indicates the presence of a clinically relevant amount of bacteria in the donor tissue and no binding indicates the absence of a clinically relevant amount of bacteria in the donor tissue.

In certain embodiments of the seventh aspect of the invention, the sample is treated prior to or concomitantly with contacting the sample with the set of binding agents. Preferably, the treatment exposes a binding site of the binding agent on the Gram-negative bacterial antigen or on the Gram-positive bacterial antigen. In certain embodiments of the seventh aspect of the invention, the donor tissue determined to have an absence of a clinically relevant amount of bacteria is transferred to a recipient mammal. Preferably, the donor mammal and the recipient mammal are of the same species. In certain preferred embodiments, the binding agents that specifically bind to a Gram-negative bacterial antigen comprise antibodies or antibody derivatives that specifically bind to a Gram-negative bacterial antigen. In certain preferred embodiments, the binding agents that specifically bind to a Gram-negative bacterial antigen comprise a molecule selected from the group consisting of a Limulus anti-lipopolysaccharide factor (LALF), a lipopolysaccharide binding protein (LBP), a bactericidal/permeability-increasing protein (BPI), and an antibiotic, such as polymixin or bacitracin. Preferably, the binding agents that specifically bind to a Gram-negative bacterial antigen specifically bind to the lipopolysaccharide structure of the Gram-negative bacteria. In certain preferred embodiments, the binding agents that specifically bind to a Gram-positive bacterial antigen comprise antibodies or antibody derivatives that specifically bind to a Gram-positive bacterial antigen. In certain embodiments, the binding agents that specifically bind to a Gram-positive bacterial antigen comprise an antibiotic, wherein the antibiotic is not vancomycin. Preferably, the binding agents that specifically bind to a Gram-positive bacterial antigen specifically bind to the lipotechoic acid structure of the Gram-positive bacteria.

In various embodiments of the seventh aspect of the invention, the binding agents that specifically bind to a Gram-negative bacterial antigen are detectably labeled with a first reporter molecule and the binding agents that specifically bind to Gram-positive bacterial antigen are detectably labeled with a second reporter molecule. In certain embodiments, the first reporter molecule and the second reporter molecule are the same. In another embodiment, the first reporter molecule and the second reporter molecule are not the same. Preferably, one or both of the first reporter molecule and the second reporter molecule is a molecule with enzymatic activity, a radio-labeled molecule, a fusion molecule, a fluorogenic molecule, a metal sol, a particle, a chromatic molecule, or a molecule that is specifically bound by a secondary binding agent.

In an eighth aspect, the invention provides a method for screening for the presence of a clinically relevant amount of Gram-positive bacteria in a donor tissue from a donor mammal for transfer to a recipient mammal, wherein the donor tissue is stored in a fluid, comprising contacting a sample of fluid with a set of binding agents, wherein the set of binding agents comprises binding agents that specifically bind to a Gram-positive bacterial antigen, and determining binding of the set of binding agents to the sample, wherein binding indicates the presence of a clinically relevant amount of Gram-positive bacteria in the donor tissue and no binding indicates the absence of a clinically relevant amount of Gram-positive bacteria in the donor tissue.

In certain embodiments of the eighth aspect of the invention, the sample is treated prior to or concomitantly with contacting the sample with the set of binding agents. Preferably, the treatment exposes a binding site for the binding agent on the Gram-positive bacterial antigen. In certain embodiments, the donor tissue determined to have an absence of a clinically relevant amount of bacteria is transferred to a recipient mammal. Preferably, the donor mammal and the recipient mammal are of the same species. In certain preferred embodiments, the binding agents that specifically bind to a Gram-positive bacterial antigen comprise antibodies or antibody derivatives that specifically bind to a Gram-positive bacterial antigen. In certain embodiments, the binding agents that specifically bind to a Gram-positive bacterial antigen comprise an antibiotic, wherein the antibiotic is not vancomycin. Preferably, the binding agents that specifically bind to a Gram-positive bacterial antigen specifically bind to the lipotechoic acid structure of the Gram-positive bacteria.

In various embodiments of the eighth aspect of the invention, the binding agents that specifically bind to a Gram-positive bacterial antigen are detectably labeled with a reporter molecule. Preferably, the reporter molecule is a molecule with enzymatic activity, a radio-labeled molecule, a fusion molecule, a fluorogenic molecule, a metal sol, a particle, a chromatic molecule, or a molecule that is specifically bound by a secondary binding agent.

In a ninth aspect, the invention provides a method for screening for the presence of a clinically relevant amount of Gram-negative bacteria in a donor tissue from a donor mammal for transfer to a recipient mammal, wherein the donor tissue is stored in a fluid, comprising contacting a sample of the fluid with a set of binding agents, wherein the set of binding agents comprises binding agents that specifically bind to a Gram-negative bacterial antigen, and determining binding of the set of binding agents to the sample, wherein binding indicates the presence of a clinically relevant amount of Gram-negative bacteria in the donor tissue and no binding indicates the absence of a clinically relevant amount of Gram-negative bacteria in the donor tissue.

In certain embodiments of the ninth aspect of the invention, the sample is treated prior to or concomitantly with contacting the sample with the set of binding agents. Preferably, the treatment exposes a binding site for the binding agent on the Gram-negative bacterial antigen. In certain embodiments, the donor tissue determined to have an absence of a clinically relevant amount of Gram-negative bacteria is transferred to a recipient mammal. Preferably, the donor mammal and the recipient mammal are of the same species. In certain preferred embodiments, the binding agents that specifically bind to a Gram-negative bacterial antigen comprise antibodies or antibody derivatives that specifically bind to a Gram-negative bacterial antigen. In certain embodiments, the binding agents that specifically bind to a Gram-negative bacterial antigen comprise a molecule selected from the group consisting of a Limulus anti-lipopolysaccharide factor (LALF), a lipopolysaccharide binding protein (LBP), a bactericidal/permeability-increasing protein (BPI), and an antibiotic, such as polymixin or bacitracin. Preferably, the binding agents that specifically bind to a Gram-negative bacterial antigen specifically bind to the lipopolysaccharide structure of the Gram-negative bacteria.

In various embodiments of the ninth aspect of the invention, the binding agents that specifically bind to a Gram-negative bacterial antigen are detectably labeled with a reporter molecule. Preferably, the reporter molecule is a molecule with enzymatic activity, a radio-labeled molecule, a fusion molecule, a fluorogenic molecule, a metal sol, a particle, a chromatic molecule, or a molecule that is specifically bound by a secondary binding agent.

In a tenth aspect, the invention provides a kit for screening for the presence of a clinically relevant amount of bacteria in a donor tissue from a donor mammal for transfer to a recipient mammal, wherein the tissue is stored in a fluid, comprising a set of binding agents, wherein the set of binding agents comprises binding agents that specifically bind to a Gram-negative bacterial antigen and binding agents that specifically bind to a Gram-positive bacterial antigen, and a means for detecting binding of the set of binding agents to a sample of the fluid, wherein binding indicates the presence of a clinically relevant amount of bacteria in the donor tissue and no binding indicates the absence of a clinically relevant amount of bacteria in the donor tissue.

In certain embodiments of the tenth aspect of the invention, the kit further comprises a means for treating the sample, wherein the treatment exposes a binding site for the binding agent on the Gram-negative bacterial antigen or on the Gram-positive bacterial antigen. In certain embodiments of the tenth aspect of the invention, the donor tissue determined to have an absence of a clinically relevant amount of bacteria is transferred to a recipient mammal. Preferably, the donor mammal from which the tissue was obtained and the recipient mammal are of the same species. In certain preferred embodiments, the binding agents that specifically bind to a Gram-negative bacterial antigen comprise antibodies or antibody derivatives that specifically bind to a Gram-negative bacterial antigen. In certain preferred embodiments, the binding agents that specifically bind to Gram-negative bacteria or an antigen thereof comprise a molecule selected from the group consisting of a Limulus anti-lipopolysaccharide factor (LALF), a lipopolysaccharide binding protein (LBP), a bactericidal/permeability-increasing protein (BPI), and an antibiotic, such as polymixin or bacitracin. Preferably, the binding agents that specifically bind to a Gram-negative bacterial antigen specifically bind to the lipopolysaccharide structure of the Gram-negative bacteria. In certain preferred embodiments, the binding agents that specifically bind to a Gram-positive bacterial antigen comprise antibodies or antibody derivatives that specifically bind to a Gram-positive bacterial antigen. In certain embodiments, the binding agents that specifically bind to a Gram-positive bacterial antigen comprise an antibiotic, wherein the antibiotic is not vancomycin. Preferably, the binding agents that specifically bind to a Gram-positive bacterial antigen specifically bind to the lipotechoic acid structure of the Gram-positive bacteria.

In various embodiments of the tenth aspect of the invention, the binding agents that specifically bind to a Gram-negative bacterial antigen are detectably labeled with a first reporter molecule and the binding agents that specifically bind to a Gram-positive bacterial antigen are detectably labeled with a second reporter molecule. In certain embodiments, the first reporter molecule and the second reporter molecule are the same. In another embodiment, the first reporter molecule and the second reporter molecule are not the same. Preferably, one or both of the first reporter molecule and the second reporter molecule is a molecule with enzymatic activity, a radio-labeled molecule, a fusion molecule, a fluorogenic molecule, a metal sol, a particle, a chromatic molecule, or a molecule that is specifically bound by a secondary binding agent.

In an eleventh aspect, the invention provides a kit for screening for the presence of a clinically relevant amount of Gram-positive bacteria in a donor tissue from a donor mammal for transfer to a recipient mammal, wherein the donor tissue is stored in a fluid, comprising a set of binding agents, wherein the set of binding agents comprises binding agents that specifically bind to a Gram-positive bacterial antigen, and a means for detecting binding of the set of binding agents to a sample of the fluid, wherein binding indicates the presence of a clinically relevant amount of Gram-positive bacteria in the donor tissue and no binding indicates the absence of a clinically relevant amount of Gram-positive bacteria in the donor tissue.

In certain embodiments of the eleventh aspect of the invention, the kit further comprises a means for treating the sample, wherein the treatment exposes a binding site for the binding agent on the Gram-positive bacterial antigen. In certain embodiments, the donor tissue determined to have an absence of a clinically relevant amount of Gram-positive bacteria is transferred to a recipient mammal. Preferably, the donor mammal and the recipient mammal are of the same species. In certain preferred embodiments, the binding agents that specifically bind to a Gram-positive bacterial antigen comprise antibodies or antibody derivatives that specifically bind to a Gram-positive bacterial antigen. In certain embodiments, the binding agents that specifically bind to a Gram-positive bacterial antigen comprise an antibiotic, wherein the antibiotic is not vancomycin. Preferably, the binding agents that specifically bind to a Gram-positive bacterial antigen specifically bind to the lipotechoic acid structure of the Gram-positive bacteria.

In various embodiments of the eleventh aspect of the invention, the binding agents that specifically bind to a Gram-positive bacterial antigen are detectably labeled with a reporter molecule. Preferably, the reporter molecule is a molecule with enzymatic activity, a radio-labeled molecule, a fusion molecule, a fluorogenic molecule, a metal sol, a particle, a chromatic molecule, or a molecule that is specifically bound by a secondary binding agent.

In a twelfth aspect, the invention provides a kit for screening for the presence of a clinically relevant amount of Gram-negative bacteria in a donor tissue from a donor mammal for transfer to a recipient mammal, wherein the donor tissue is stored in a fluid, comprising a set of binding agents, wherein the set of binding agents comprises binding agents that specifically bind to a Gram-negative bacterial antigen, and a means for detecting binding of the set of binding agents to a sample of the fluid, wherein binding indicates the presence of a clinically relevant amount of Gram-negative bacteria in the donor tissue and no binding indicates the absence of a clinically relevant amount of Gram-negative bacteria in the donor tissue.

In certain embodiments of the twelfth aspect of the invention, the kit further comprises a means for treating the sample, wherein the treatment exposes a binding site for the binding agent on the Gram-negative bacterial antigen. In certain embodiments, the tissue determined to have an absence of a clinically relevant amount of Gram-negative bacteria is transferred to a recipient mammal. Preferably, the donor mammal and the recipient mammal are of the same species. In certain preferred embodiments, the binding agents that specifically bind to a Gram-negative bacterial antigen comprise antibodies or antibody derivatives that specifically bind to a Gram-negative bacterial antigen. In certain preferred embodiments, the binding agents that specifically bind to a Gram-negative bacterial antigen comprise a molecule selected from the group consisting of a Limulus anti-lipopolysaccharide factor (LALF), a lipopolysaccharide binding protein (LBP), a bactericidal/permeability-increasing protein (BPI), and an antibiotic, such as polymixin or bacitracin. Preferably, the binding agents that specifically bind to a Gram-negative bacterial antigen specifically bind to the lipopolysaccharide structure of the Gram-negative bacteria.

In various embodiments of the twelfth aspect of the invention, the binding agents that specifically bind to a Gram-negative bacterial antigen are detectably labeled with a reporter molecule. Preferably, the reporter molecule is a molecule with enzymatic activity, a radio-labeled molecule, a fusion molecule, a fluorogenic molecule, a metal sol, a particle, a chromatic molecule, or a molecule that is specifically bound by a secondary binding agent.

In various embodiments of the seventh, eighth, ninth, tenth, eleventh, and twelfth aspects of the invention, the donor tissue is preferably lung, heart, liver, skin, kidney, pancreas, spleen, or bone marrow.

In certain preferred embodiments of all of the above aspects of the invention, the set of binding agents is immobilized on a solid-phase support (e.g., a micro-titer plate).

In preferred embodiments of the first, second, third, fourth, fifth, sixth, seventh, eighth, ninth, tenth, eleventh, and twelfth aspects of the invention, the donor and/or recipient mammal is a human or a domesticated mammal.

BRIEF DESCRIPTION OF THE DRAWINGS

FIG. 3A shows the device absent addition of a sample of blood or a blood product (or absent the addition of a fluid in which a donor tissue is stored). FIG. 3B shows the device at the point in time when the sample of blood or blood product is added. FIG. 3C shows the contact of the sample of bodily fluid with the device. FIG. 3D shows a positive result using the device according to the invention, indicating the sample of blood or blood product tested was contaminated with a micro-organism.

FIGS. 4A–4D are schematic representations of a method according to the invention. FIG. 4A shows the addition of a sample of blood, blood product, or fluid in which donor tissue is stored to the test device. FIG. 4B shows the addition of a latex beads coated with antibodies that specifically bind to both Gram-negative and Gram-positive bacteria to the test device. FIG. 4C shows the mixing of the sample with the antibody-coated latex beads in the test device. FIG. 4D show the visual results of negative binding (i.e., no bacteria in the sample; left) and binding (i.e., presence of bacteria in the sample; right).

DETAILED DESCRIPTION OF THE PREFERRED EMBODIMENTS

Figure 1:
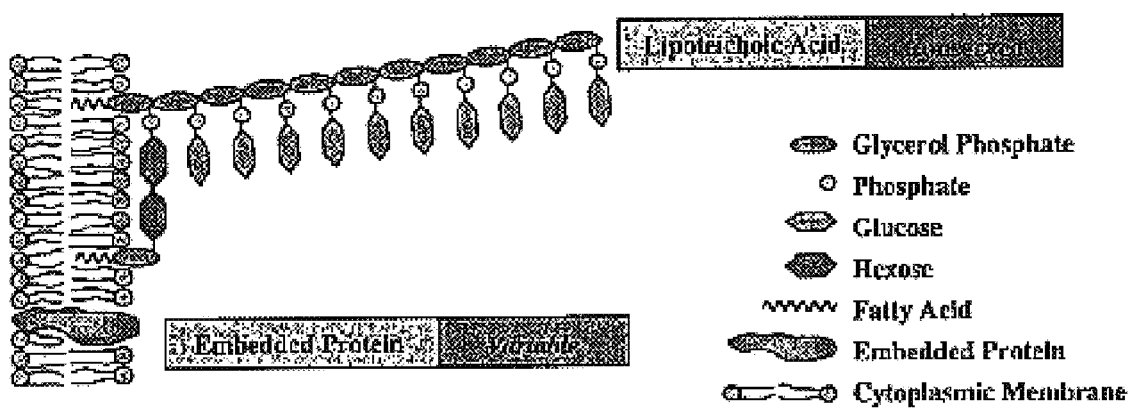
FIG. 1 is a schematic representation of a typical Gram-positive cell wall membrane.

The invention relates to the detection of a clinically relevant amount of a contaminating bacteria in blood or a blood product or a donor tissue, particularly donated blood or a blood product or donated tissue that is transferred from a donor individual to a recipient individual. The invention provides rapid antigen binding-based methods and kits for detecting clinically relevant amounts of micro-organisms in blood or a blood products or in the fluid in which a donor tissue is stored. The invention arises from the recognition that the exact identity of the contaminating bacteria in the donor blood or a blood product or the donor tissue to be used for transfusion or transplantation is irrelevant. Accordingly, the invention provides methods using binding agents that specifically bind to both Gram-positive and Gram-negative bacteria to detect any binding to a sample of blood or a blood product or to a sample of a fluid in which a donor tissue is stored. Thus, if any binding is detected, the blood or blood product or donor tissue is known to be contaminated, and will preferably not be used for transfer to another individual.

The published patent and scientific literature referred to herein establishes knowledge that is available to those with skill in the art. The issued patents, applications, and references that are cited herein are hereby incorporated by reference to the same extent as if each was specifically and individually indicated to be incorporated by reference. Any inconsistency between these publications and the present disclosure shall be resolved in favor of the present disclosure.

In a first aspect, the invention provides a method for screening for the presence of a clinically relevant amount of bacteria in donor blood or a donor blood product from a donor mammal for transfer to a recipient mammal. The method comprises contacting a sample of blood or a blood product with a set of binding agents, wherein the set of binding agents comprises binding agents that specifically bind to a Gram-negative bacterial antigen and binding agents that specifically bind to a Gram-positive bacterial antigen, and determining binding of the set of binding agents to the sample, wherein binding indicates the presence of a clinically relevant amount of bacteria in the donor blood or blood product and no binding indicates the absence of a clinically relevant amount of bacteria in the donor blood or blood product. In preferred embodiments, the donor and/or recipient mammal is a human or a domesticated mammal (e.g., a cat, dog, horse, pig).

As used herein, "blood or blood product" includes any cell found in blood or bone marrow, as well as any product derived from the blood or bone marrow including, without limitation, whole blood, red blood cells, platelets, serum, plasma, hematopoietic stem cells, and leukocytes (including lymphocytes). The ordinarily skilled biologist will understand that without addition of anti-clotting agents such as EDTA or heparin, whole blood will clot, rendering the majority of the blood cells unusable in transfusion. Accordingly, included in the term, "blood or blood product," is blood treated with any anti-clotting agent. In addition, during the isolation of particular blood products (e.g., platelets using platelet-phoresis), non-blood components, such as physiological saline may be added to the blood. Accordingly, also included in the term, "blood or blood product," is blood to which has been added any biologically inert substance, such as physiological saline, water, or a storage nutrient solution.

As used herein, the term "clinically relevant amount" is used to mean an amount of bacteria contamination in a blood or blood product that is equal to or higher than an amount that, when present in a blood or blood product transfused into the typical transfusion recipient, induces, without limitation, any one of the following symptoms in the transfused recipient: fever, chills, hypotension, nausea/vomiting, headache, dyspnea, oliguria, diarrhea, pain at site of infusion, urticaria, sweating, chest pain, petecchiae and ecchymosis, disseminated intravascular coagulation, septic shock, organ failure, and death. (See, e.g., Morduchowicz, G. et al., Reviews of Infectious Diseases 13: 307 (1991)). Because of the rapid division time of bacteria, the amount of bacteria in the blood should be determined as close to the transfusion time as possible. Typically, at the time of transfusion, a clinically relevant amount is greater than $1 \times 10^7$ colony forming units (CFU) per ml of the blood or blood product. Preferably, at the time of transfusion, a clinically relevant amount is greater than $1 \times 10^6$ CFU/ml. More preferably, at the time of transfusion, a clinically relevant amount is greater than $1 \times 10^5$ CFU/ml. Even more preferably, at the time of transfusion, a clinically relevant amount is greater than $1 \times 10^4$ CFU/ml. Even more preferably, at the time of transfusion, a clinically relevant amount is greater than $1 \times 10^3$ CFU/ml. Most preferably, at the time of transfusion, a clinically relevant amount is greater than $1 \times 10^2$ CFU/ml. Of course, one of ordinary skill in the transfusion medicine industry will recognize that although some individuals, such as severely immunocompromised patients or newborns, will have an immune system that is unable to clear an amount of bacteria that is below a clinically relevant amount. However, the ordinarily skilled practitioner will understand that the methods of the invention will suffice for testing of blood and blood products to be used for transfusion in the vast majority of patients.

As used herein, "specifically binds" means that a binding agent (e.g., an antibody) recognizes and binds to a particular ligand (e.g., a polypeptide, carbohydrate, lipid, or glycoprotein), but does not substantially recognize and bind to other molecules in a sample, e.g., a biological sample that naturally includes many different proteins. Likewise, a ligand bound by a binding agent that specifically binds that ligand is said to be "specifically bound" by that binding agent. The association formed between the binding agent and its ligand may be covalent, and is preferably noncovalent. Preferably, a binding agent that specifically binds a ligand forms an association with that ligand with an affinity of at least $10^6$ M$^{-1}$, more preferably, at least $10^7$ M$^{-1}$, even more preferably, at least $10^8$ M$^{-1}$, and most preferably, at least $10^9$ M$^{-1}$ either in water, under physiological conditions, or under conditions which approximate physiological conditions with respect to ionic strength, e.g., 140 mM NaCl, 5 mM MgCl$_2$.

As used herein, by "antigen" (for example, a Gram-negative bacterial antigen or a Gram-positive bacterial antigen) is meant any molecule, with the exception of nucleic acid molecules and peptidoglycans, in any structural conformation which may be specifically bound by a binding agent. For example, a Gram-negative bacterial antigen is an antigen that is secreted by, internal to, or present on (or through) the cell membrane, cell wall, or periplasmic space of a Gram-negative bacterium. The site on the antigen which is bound by the binding agent is called a "binding site." An antigen may be, without limitation, a protein, a glycoprotein, a carbohydrate, or a lipid. Specifically excluded from the definition of antigen in accordance with the present invention are peptidoglycans and nucleic acid molecules, such as DNA or RNA.

As used herein, by "Gram-positive bacteria" is meant a strain, type, species, or genera of bacteria that, when exposed to the Gram stain, retains the dye and is, thus, stained blue-purple.

As used herein, by "Gram-negative bacteria" is meant a strain, type, species, or genera of bacteria that, when exposed to the Gram stain does not retain the dye and is, thus, is not stained blue-purple. The ordinarily skilled practitioner will recognize, of course, that depending on the concentration of the dye and on the length of exposure, a Gram-negative bacteria may pick up a slight amount of Gram stain and become stained light blue-purple. However, in comparison to a Gram-positive bacteria stained with the same formulation of Gram stain for the same amount of time, a Gram-negative bacteria will be much lighter blue-purple in comparison to a Gram-positive bacteria.

The bacterial cell wall is a complex, semi-rigid structure, which defines the shape of the organism, surrounds the underlying fragile cytoplasmic membrane, and protects the bacterial cell from the external environment The bacterial cell wall is composed of a macromolecular network known as the peptidoglycan, comprising carbohydrates and polypeptides that form a lattice around the bacterial cell. The bacterial cell wall provides the mechanical stability for the bacterial cell and prevents osmotic lysis. Most relevant to the present invention, it is the chemical composition of the cell wall that is used to differentiate the major species of bacteria.

The cell walls of different species of bacteria may differ greatly in thickness, structure and composition. However, there are two predominant types of bacterial cell wall, and whether a given species of bacteria has one or the other type of cell wall can generally be determined by the cell's reaction to certain dyes. Perhaps the most widely-used dye for staining bacteria is the Gram stain. When stained with this crystal violet and iodine stain, bacteria which retain the stain are called Gram-positive, and those that do not are called Gram-negative.

The Gram-positive bacterial cell wall contains a relatively thick coat of peptidoglycan. This structure is arranged as repeat carbohydrate units of N-acetylglucosamine (NAG) and N-acetylmuramic (NAM) acid linked by β-1,4 glycosidic bonds. The N-acetylmuramic acid residues are crosslinked to adjacent (NAM-NAG)$_x$ chains (where x=any number) via tetrapeptides where peptides 2 and 3 may show some variability in the nature of the peptide. Some of the cross-links extend above and below the plane making multiple layers of the peptidoglycan. These polymers surround the surface of the cell thereby defining the shape of the organism.

Located within the Gram-positive cell wall is a lipopolymer compound containing lipoteichoic acids (LTA) that may make up considerable mass of the cell walls of some species. These polymers are comprised of primarily glycerol (or ribitol) phosphate. FIG. 1 shows a schematic representation of a typical Gram-positive bacterial cell wall membrane. Because of their high polarity and net positive charge, lipoteichoic acid structures are believed to regulate ion and nutrient flow into and out of the bacterial cell. LTA structures are highly antigenic and can form the basis of the molecular specificity required to enable broad-based detection of this class of bacteria. Because lipoteichoic acids are common in Gram-positive bacteria, test procedures that recognized this structure would be highly indicative of Gram-positive bacterial contamination. Since the chemical structure of the lipoteichoic acid polymers is reasonably conserved among the various strains of Gram-positive bacteria, probing for the presence of this cell wall structure allows the detection of multiple Gram-positive bacteria.

The Gram-negative-type bacterial cell wall is distinctly layered in appearance and is much thinner than the Gram-positive cell wall. The Gram-negative bacterial cell wall is similar to that of the Gram-positive in that it is built on a protein containing lipid bilayer; however, the inward facing lipids are phospholipids, whereas the outward facing lipids include macromolecules called lipopolysaccharides (LPS). This LPS structure creates a strong negative charge on the outside surface of the cell, which is used for organism recognition and survival. This LPS structure also provides the toxic effect of a Gram-negative infection and for this reason is also called "endotoxin".

Figure 2:
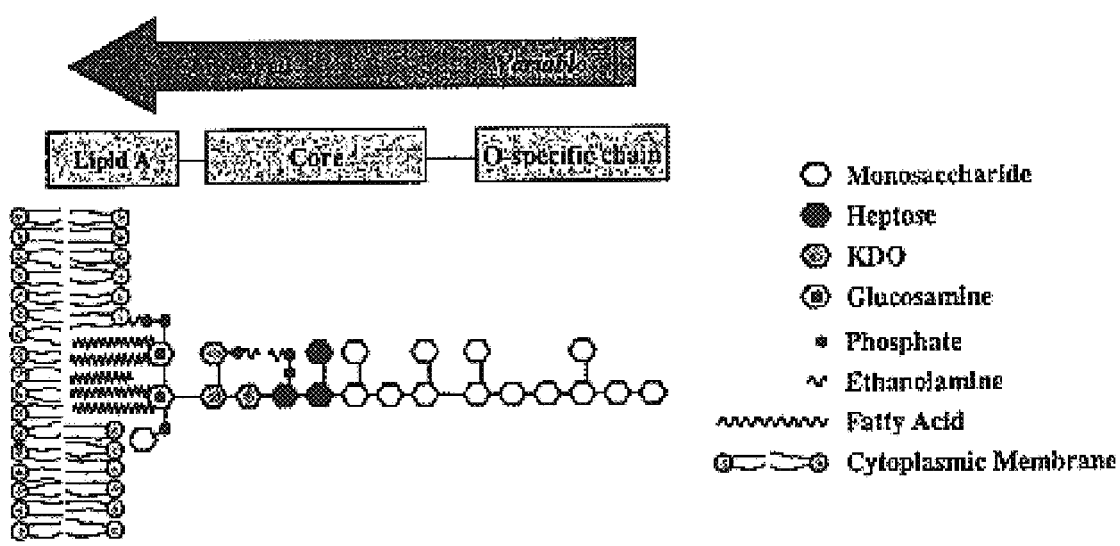
FIG. 2 is a schematic representation of the structure of lipopolysaccharide (LPS) found in the cell wall of Gram-negative bacteria.
Figure 3A:
FIGS. 3A–3D are schematic representations of a device according to an embodiment of the invention.
Figure 3B:
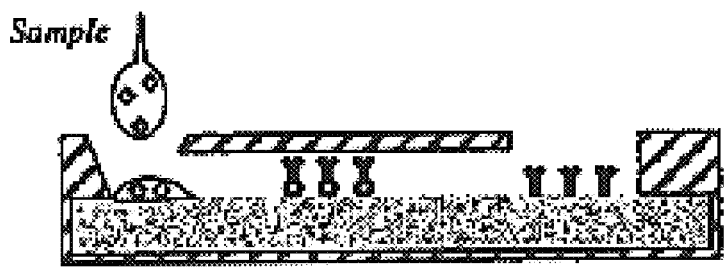
Figure 3C:
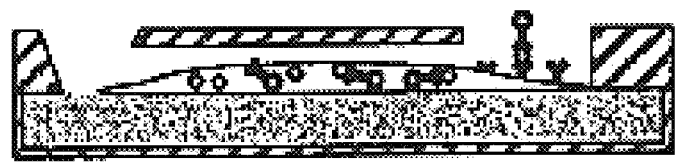
Figure 3D:
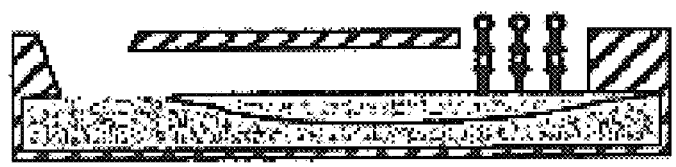

The structure of the LPS component has been described in numerous studies and is shown in FIG. 2. In general the LPS antigen structure can be described as containing three distinct regions. The outermost region, which is called the O-specific region and consists of linear or branched chains of carbohydrates, is highly variable and is typically distinct in individual species. Serology tests utilize this difference to enable identification of particular strains of Gram-negative bacteria. The presence of the O-chains create an appearance of a smooth surface on microscopic examination. In contrast, those species or mutants without the O-specific side chains appear rough. Most wild types are therefore termed as "smooth" strains, whereas mutants without this structure are termed "rough" strains.

Internal to the O-specific region in the LPS structure is the core polysaccharide region, which shows a high degree of homology between genera. The core region can be further divided into two regions the "inner core" and the "outer core". The outer core of the core region exhibits some variability but has common elements, and generally contains glucose, galactose, N-acetyl-glucosamine, and other carbohydrates. The inner core of the core region of all LPS expressing Gram-negative bacteria contains chemically identical structures. The inner core is comprised of heptose and 2-Keto-3-deoxy-octonate (KDO) residues.

The internal most component of the LPS structure is the Lipid A structure, which constitutes the chemically most uniform portion of the LPS. Lipid A is comprised of a β-glucosaminyl-(1→6)-α-glucosamine disaccharide that is phosphorylated at each of its distal carbohydrate termini. The carbohydrate backbone is acylated at each of the 2,3 centers by substituted myristic acid derivatives. The fatty acid side chains show some minor degrees of species dependent modification, but these fatty acids are incorporated into the cell membrane and are not available for immuno-recognition. Antibody generation is likely to be a result of the surfaced exposed bisphosphoryl-glucosamine disaccharide backbone structure that is highly conserved.

The structural variability of the LPS structure decreases from the surface exposed O-specific region to the inner and outer core regions to the disaccharide derivative and membrane embedded lipid A component. The reason for this gradient of variability is believed to be the evolutionary pressure exerted towards the Gram-negative bacteria. It is conceivable that the microbes changed their exposed surface structure over time to respond to this pressure.

As with the lipoteichoic acid structures in Gram-positive bacteria, the conserved lipopolysaccharide structures between genera in Gram-negative bacteria can be used as a methodology for broad-based detection. These unique targets (lipoteichoic acids in Gram-positive and Lipid A or core regions of the LPS structure of Gram-negative) are the basis of the microorganism class detection methodology.

As used herein, a "binding agent" is a molecule or macromolecule capable of binding to a ligand. Preferably, the binding agent of the invention is not a recombinant agent derived from an agent present in horseshoe crab (e.g., *Limulus polyphemus*) that binds to endotoxin. Even more preferably, the binding agent of the invention is not a naturally-occurring agent present in horseshoe crab (e.g., *Limulus polyphemus*) that binds to endotoxin. A binding agent may be, without limitation, an antibody, an antibiotic, a protein, a fusion protein (i.e., a protein comprising portions of two or more proteins), or a chemical chelator. In certain preferred embodiments, a binding agent according to the invention is a peptide or a peptidomimetic. For purposes of the invention, a "peptide" is a molecule comprised of a linear array of amino acid residues connected to each other in the linear array by peptide bonds. Such peptides according to the invention may include from about three to about 500 amino acids, and may further include secondary, tertiary or quaternary structures, as well as intermolecular associations with other peptides or other non-peptide molecules. Such intermolecular associations may be through, without limitation, covalent bonding (e.g., through disulfide linkages), or through chelation, electrostatic interactions, hydrophobic interactions, hydrogen bonding, ion-dipole interactions, dipole-dipole interactions, or any combination of the above.

In certain preferred embodiments, such a binding agent comprises a complementarity determining region (CDR) of an antibody which binds under physiological conditions to an antigen-containing epitope of a lipopolysaccharide (LPS) structure of a Gram-negative bacteria or a lipotechoic acid (LTA) structure of a Gram-positive bacteria or a peptidomimetic of such a complementarity determining region. For purposes of the invention, a "complementarity determining region of an antibody" is that portion of an antibody which binds under physiological conditions to an epitope, including any framework regions necessary for such binding, and which is preferably comprised of a subset of amino acid residues encoded by the human heavy chain V, D and J regions, the human light chain V and J regions, and/or combinations thereof. Examples of such preferred embodiments include an antibody, or an antibody derivative, which may more preferably be a monoclonal antibody, a human antibody, a humanized antibody, a single-chain antibody, a chimeric antibody, or an antigen-binding antibody fragment.

Those skilled in the art are enabled to make any such antibody derivatives using standard art-recognized techniques. For example, Jones et al. (Nature 321: 522–525 (1986)) discloses replacing the CDRs of a human antibody with those from a mouse antibody. Marx (Science 229: 455–456 (1985)) discusses chimeric antibodies having mouse variable regions and human constant regions. Rodwell (Nature 342: 99–100 (1989)) discusses lower molecular weight recognition elements derived from antibody CDR information. Clackson (Br. J. Rheumatol. 3052: 36–39 (1991)) discusses genetically engineered monoclonal antibodies, including Fv fragment derivatives, single chain antibodies, fusion proteins chimeric antibodies and humanized rodent antibodies. Reichman et al. (Nature 332: 323–327 (1988)) discloses a human antibody on which rat hypervariable regions have been grafted. Verhoeyen et al. (Science 239: 1534–1536 (1988)) teaches grafting of a mouse antigen binding site onto a human antibody.

In addition, those skilled in the art are enabled to design and produce peptidomimetics having binding characteristics similar or superior to such complementarity determining region (see e.g., Horwell et al., Bioorg. Med. Chem. 4: 1573 (1996); Liskamp et al., Recl. Trav. Chim. Pays-Bas 1: 113 (1994); Gante et al., Angew. Chem. Int. Ed. Engl. 33: 1699 (1994); Seebach et al., Helv. Chim. Acta 79: 913 (1996)). Accordingly, all such antibody derivatives and peptidomimetics thereof are contemplated to be within the scope of the present invention Compositions according to the invention may further include physiologically acceptable diluents, stabilizing agents, localizing agents or buffers.

Additional preferred binding agents according to the invention include small molecules, which can be identified using screening or rational design approaches as discussed later herein.

Most preferably, the binding agents of the present invention are antibodies, such as polyclonal antibodies or monoclonal antibodies, and/or antibody derivatives. Generation of monoclonal and polyclonal antibodies is well-within the knowledge of one of ordinary skill in the art of biology (see, e.g., Ausubel et al., Current Protocols in Molecular Biology, John Wiley & Sons, New York, N.Y., 1994). A number of procedures are useful in producing antibodies to the desired unique target antigens. Traditional immunization and harvesting techniques will result in the creation of polyclonal antibodies directed against the common determinants of the target bacterial species (LTA or LPS). Additionally, cellular hybridization techniques can be utilized to produce immortal hybridoma cell lines that generate specific monoclonal antibodies to the target species.

Antibodies having potential utility for broadly detecting Gram-positive bacteria include those described in Fisher et al., PCT Publication No. WO98/57994; Jackson, D. E. et al., Infection and Immunity 43: 800 (1984); Hamada, S. et al, Microbiol. Immunol. 28: 1009 (1984); Aasjord, P. et al., Acta Path. Microbiol. Immunol. Scand. Sect. C, 93: 245 (1985); McDaniel, L. S. et al., Microbial Pathogenesis 3: 249 (1987); Tadler, M. B. et al., Journal of Clinical Laboratory Analysis 3: 21 (1989); and Stuertz, K et al., Journal of Clinical Microbiology 36: 2346 (1998).

Antibodies having potential utility for broadly detecting Gram-negative bacteria include those described in Nelles, M. J. et al, Infect. Immun. 46: 677 (1984); Teng, N. N. H. et al, Proc. Natl. Acad. Sci. USA 82: 1790 (1985); Dunn, D. L. et al., Surgery 98: 283 (1985); De Jongh-Leuvenink, J. et al, Eur. J. Clin. Microbiol. 5: 148 (1986); Bogard, W. C. et al., Infect. Immun. 55: 899 (1987); Pollack, M. et al., Bacterial Endotoxins: Pathophysiological Effects, Clinical Significance, and Pharmacological Control. pp. 327–338 Alan R. Liss, Inc. (1988); Priest, B. P. et al., Surgery 106: 147 (1989); Tyler, J. W. et al., Journal of Immunological Methods 129: 221 (1990); Siegel, S. A. et al., Infect. Immun. 61: 512 (1993); Shelburne, C. E. et al., J. Periodont. Res. 28: 1 (1993); Di Pardova, F. E. et al., Infect. Immun. 61: 3863 (1993); and De Kievit, T. R. and Lam, J. S. J. Bacteriol. 176: 7129 (1994).

The selection as to which antibody(ies) to use can be done through classical techniques. Antibody specificity, binding extent and kinetics can be characterized by empirically testing each antibody in an empirical format. Micro-titer screening formats are well documented in the literature to aid in characterizing specific antibody response in any given immunoassay format. Likewise, the activities of detectably labeled antibodies can be characterized by executing a variety of chemical conjugation techniques and screening the resulting product for the optimal performance parameters. The capture antibody and detectably labeled antibody can be screened against the clinical isolates of bacteria from retained platelet or red cell samples to emulate final assay performance as close to final product embodiment as possible. This experimentation leads to the selection and optimization of antibody reagents for application in the various assay formats described below. If binding agents are identified which empirically perform better than the antibody alternatives described or generated, then they are evaluated in the same empirical format described for the antibodies.

Monoclonal antibodies with specificity towards the unique cross-genus targets on the bacterial cell surfaces are utilized to develop a class detection assay format. If single antibody clones do not impart the detection sensitivity limit desired (such as may be the case with substitutions on the LTA structure) for each species, blends of monoclonal antibodies could be utilized. Extensions beyond this for LPS could include the creation of polyclonal antisera with broad specificity across the different Gram-negative species. Polyclonal antibodies can also be substituted in each of the described assay formats below.

Yet another type of binding agent of the invention are binding receptors that are distinct from immunoglobulins.

Certain preferred methods utilize the complexation of Gram-negative bacteria with such non-limiting species as Limulus anti-lipopolysaccharide factor (LALF), polymixins, Cationic Antimicrobial Protein (CAP18), Serum Myloid P, magainins, bactenecins, Toll-Like Receptor 4 (TLR-4), Lipopolysaccharide Binding Protein (LBP) and Bactericidal/permeability-increasing protein (BPI), as well as antibiotics such as Bacitracin and other antibiotics. Certain preferred methods utilize the complexation of Gram-positive bacteria with such non-limiting species as mannose binding protein (MBP), Toll-Like Receptor 2 (TLR-2), histatins, and antibiotics (e.g., gentamycin), where the antibiotic is not vancomycin. Certain preferred methods utilize the complexation of both Gram-negative and Gram-positive bacterial with such non-limiting species as CD14, α-helical cationic peptides, lactoferricin B, platelet microbial proteins, and neutrophil peptides (Defensins). Each of these binding agents has the ability to bind to broad genera of bacteria and could be utilized in tandem or as an alternative to the immune complexation reagents.

The antibodies and binding agents indicated above can be utilized as described or modified as necessary to produce a useful immunological reagent.

According to the first aspect of the invention, the presence or absence of binding may be determined according to standard techniques, including the use of binding assays according to the invention, as described below. In general, a determination of "binding" (i.e., presence of a clinically relevant of bacteria in the blood or blood product) is found when the sample from the donor binds at least 0.5× higher than background binding, where the background is a sample of blood or blood product that is free from any bacteria contamination. For example, a sample of donor platelets is compared to a background comprising a sample of platelets that is free from any bacteria contamination. Thus, where the background is 0.1 units (e.g., as determined by a micro-titer plate reader), a determination of "binding" is found when the sample from the donor blood or blood product is at least 0.15 units. More preferably, a determination of "binding" is found when the sample from the donor binds at least 0.75× higher than background binding. Even more preferably, a determination of "binding" is found when the sample from the donor binds at least 1.0× higher than background. Yet more preferably, a determination of "binding" is found when the sample from the donor binds at least 1.25× higher than background. Most preferably, a determination of "binding" is found when the sample from the donor binds at least 1.5× higher than background.

In certain embodiments of the first aspect of the invention, the sample is treated prior to or concomitantly with contacting the sample with the set of binding agents. Preferably, the treatment exposes a binding site for the binding agent on the Gram-negative bacterial antigen or on the Gram-positive bacterial antigen. A binding site on a bacterial antigen may be exposed by, for example, cleaving an antigen from the cell wall or cell membrane of the bacteria, thereby exposing the binding site; inducing the bacteria to secrete the antigen, thereby exposing the binding site; lysing the bacteria, thereby releasing an intracellular bacterial antigen and thus exposing the binding site on the antigen; or by inducing a conformational change on the bacterial antigen, thereby exposing the binding site. Such treatments include mechanical disruption of the bacterial cells in the sample by physical means, including, without limitation, sonication, boiling, or homogenization using, for example, a Dounce homogenizer. The treatment may also be treatment of the sample by chemical means with a compound or composition, such as detergent, a basic solution (for alkaline lysis), an acidic solution (for acidic lysis), EDTA, EGTA, a metal ion, an anion, a cation, a surfactant, a chelator, and/or an enzyme, the treatment exposes a binding site for the binding agent on the Gram-negative bacterial antigen or on the Gram-positive bacterial antigen.

In one embodiment of the first aspect of the invention, the donor blood or blood product determined to have an absence of a clinically relevant amount of bacteria is transferred to a recipient mammal. By "transfer" is meant the administration, transfusion, transplantation, or transmittance of the blood, blood product, and/or tissue from a donor mammal to a recipient mammal Preferably, the donor mammal from which the sample of blood or blood product was obtained and the recipient mammal are of the same species. According to the methods of the present invention, donor blood or a donor blood product may be rapidly screened for the presence of any contaminating bacteria, regardless of the strain or type of the contaminating bacteria It will be understood that given the rapid propagation rate of bacteria in blood or a blood product, it is preferable to transfuse the intended recipient with the donor blood or blood product lacking a clinically relevant amount of bacteria, as determined according to the invention, shortly following testing. Preferably, the clinically relevant amount of bacteria-free donor blood or blood product is administered as a transfusion to the patient not more than 42 days following the initiation of testing, more preferably, not more than 30 days post-testing, more preferably, not more than 2 weeks post-testing, more preferably, not more than 7 days post-testing, still more preferably, not more than 3 days post testing, even more preferably, not more than 2 days post testing, even more preferably, not more than 24 hours post-testing, even more preferably, not more than 12 hours post-testing, even more preferably, not more than 6 hours post-testing, and most preferably, the donor blood or blood product found to lack a clinically relevant amount of bacteria is transfused into the recipient within 3 hours of the initiation of testing. Most preferably, the blood or blood product is whole blood, hematopoietic stem cells, leukocytes, platelets, red blood cells, plasma, or serum.

In certain preferred embodiments, the binding agents that specifically bind to a Gram-negative bacterial antigen comprise antibodies or antibody derivatives that specifically bind to a Gram-negative bacterial antigen. In certain preferred embodiments, the binding agents that specifically bind to a Gram-negative bacterial antigen comprise a molecule selected from the group consisting of a Limulus anti-lipopolysaccharide factor (LALF), a lipopolysaccharide binding protein (LBP), a bactericidal/permeability-increasing protein (BPI), and an antibiotic, such as polymixin or bacitracin. Preferably, the binding agents that specifically bind to Gram-negative bacterial antigen specifically bind to the lipopolysaccharide structure of the Gram-negative bacteria.

In certain preferred embodiments, the binding agents that specifically bind to Gram-positive bacterial antigen comprise antibodies or antibody derivatives that specifically bind to Gram-positive bacterial antigen. In certain embodiments, the binding agents that specifically bind to Gram-positive bacterial antigen comprise an antibiotic, wherein the antibiotic is not vancoymycin. Preferably, the binding agents that specifically bind to Gram-positive bacterial antigen specifically bind to the lipotechoic acid structure of the Gram-positive bacteria.

The ordinarily skilled biologist will understand that any combination of one or more different binding agents may be employed in the invention. Thus, an antibiotic that specifically binds a subset of Gram-positive bacteria may be combined with an antibody that specifically binds to the remaining Gram-positive bacteria and a second antibody that specifically binds to all Gram-negative bacteria.

In various embodiments of the first aspect of the invention, the binding agents that specifically bind to a Gram-negative bacterial antigen are detectably labeled with a first reporter molecule and the binding agents that specifically bind to a Gram-positive bacterial antigen are detectably labeled with a second reporter molecule. In one embodiment, the first reporter molecule and the second reporter molecule are the same. In another embodiment, the first reporter molecule and the second reporter molecule are not the same. Preferably, one or both of the first reporter molecule and the second reporter molecule is a molecule with enzymatic activity, a radio-labeled molecule, a fusion molecule, a fluorogenic molecule, a metal sol (e.g., gold sot or silver sol), a particle, a chromatic molecule, or a molecule that is specifically bound by a secondary binding agent. By "secondary binding agent" meant a binding agent that specifically binds the binding agent that specifically binds Gram-negative bacteria, Gram-positive bacteria, or both.

For example, where the binding agents that specifically bind Gram-negative bacteria and Gram-positive bacteria are all murine monoclonal antibodies, a secondary binding agent may be an anti-murine antibody.

For example, a sample may be tested by FACScan analysis with the binding agents that specifically bind a Gram-positive bacterial antigen detectably labeled with FITC and the binding agents that specifically bind Gram-negative bacterial antigen detectably labeled with rhodamine. By screening for FITC and/or rhodamine staining, the sample may be determined to have no Gram-positive bacterial contamination, but may be found to have a clinically relevant level of Gram-negative bacterial contamination. Preferably, were this sample from a donor blood or blood product unit, the unit would not be used for transfusion.

The covalent coupling of a reporter molecule to a binding agent (such as an antibody or antibiotic) results in that binding agent being delectably labeled. The predominantly used reporter molecule in most immunoassay formats used today is a molecule with enzymatic activity. Binding agents are typically chemically coupled to enzymes. This produces a complex that retains immunological binding capability yet at the same time enables increased detection limits by utilizing the amplification capability of the enzyme/substrate pair. Well over 20 different enzymes labels have been reported in the literature for enzyme conjugate production. Horseradish peroxidase, alkaline phosphatase and β-galactosidase are by far the most commonly utilized. The desired characteristics for an enzyme label includes, high specific activity, small size, reaction products are easily measured and stability of the complex. Horseradish peroxidase has been utilized with a hydrogen peroxide substrate and the following dyes; Ortho-phenylene diamine (OPD), Tetra-methylbenzidine (TMB), and Di-aminobenzidine (DAB). Alkaline phosphatase has been used with Para-nitrophenyl-phosphate (PNPP) and methyl-umbelliferone. β-galactosidase uses O-Nitrophenyl β-D-galactopyranoside (ONPG) as its substrate.

Where the reporter molecule is an enzyme, enzymatic activity is dependent on the ability of the enzymatically active detectably labeled binding agent to specifically bind to the target ligand (e.g., LPA or LTA). The linkage of the enzyme to the antibody should not significantly affect the capability of the binding agent to specifically bind to its target, and should not significantly affect the catalytic activity of the enzyme. Typical cross-linking reactions utilize some type of hetero- or homo-bifunctional reagent to chemically bind the two species together. Commercially available systems exist today that can be readily employed by non-specialists.

Alternatives to the enzyme labels as reporter molecules are particle labels. These can include latex particles; dye impregnated latex particles and metal particles such as gold or silver. Particle conjugates are convenient for visual end-point assays. Commercially available particles come in the nanometer to micrometer range of sizes. Size of particle is important since it influences the endpoint detection. Latex particles as well as metal particles are available with various chemically reactive moieties on the surface. The manufacturers prepare these so that alternative conjugation procedures may be employed.

Thus, a binding agent of the invention may be detectably labeled with a reporter molecule via intermolecular association, or may be detectably labeled via intermediate molecules to the reporter molecule by intermolecular association. Such intermolecular associations may be through, without limitation, covalent bonding (e.g., through disulfide linkages), or through chelation, electrostatic interactions, hydrophobic interactions, hydrogen bonding, ion-dipole interactions, dipole-dipole interactions, or any combination of the above. Preferred reporter molecules include, without limitation, radioisotopes, heavy metals, fluorescent labels, chromatic labels, chemoluminescent labels, enzymes and enzyme substrates. Preferred biological samples include blood, serum, plasma, red blood cells, platelets, and white blood cells. In certain preferred embodiments, the method according to this aspect of the invention takes the form of a conventional immunoassay, such as ELISA or RIA. In another preferred embodiment, the method employs either direct or indirect immunofluorescence.

In a preferred embodiment of the first aspect of the invention, the set of binding agents is immobilized on a solid-phase support (e.g., a micro-titer plate).

In a second aspect, the invention provides method for screening for the presence of a clinically relevant amount of Gram-positive bacteria in donor blood or a blood product from a donor mammal for transfer to a recipient mammal. The method comprises contacting a sample of the donor blood or a blood product with a set of binding agents, wherein the set of binding agents comprises binding agents that specifically bind to Gram-positive bacterial antigen, and determining binding of the set of binding agents to the sample, wherein binding indicates the presence of a clinically relevant amount of Gram-positive bacteria in the donor blood or blood product and no binding indicates the absence of a clinically relevant amount of Gram-positive bacteria in the donor blood or blood product. Preferably, the donor and/or recipient mammal is a human or a domesticated mammal.

In a third aspect, the invention provides a method for screening for the presence of a clinically relevant amount of Gram-negative bacteria in donor blood or a blood product from a donor mammal for transfer to a recipient mammal The method in accordance with this aspect of the invention comprises contacting a sample of blood or a blood product with a set of binding agents, wherein the set of binding agents comprises binding agents that specifically bind to Gram-negative bacterial antigen, and determining binding of the set of binding agents to the sample, wherein binding indicates the presence of a clinically relevant amount of Gram-negative bacteria in the donor blood or blood product and no binding indicates the absence of a clinically relevant amount of Gram-negative bacteria in the donor blood or blood product. Preferably, the donor and/or recipient mammal is a human or a domesticated mammal.

In accordance with the second and third aspects of the invention, the terms, "binding," "antigen," "blood or blood product," "Gram-positive bacteria," "Gram-negative bacteria," "clinically relevant amount," "specifically binds," and "binding agent" are defined above. It should be noted that the methods of the first, second, and third aspects of the invention can be performed at the time of testing for ABO match, Rh match, and/or MHC match between donor and recipient mammal.

In certain embodiments of the second and third aspects of the invention, the sample is treated prior to or concomitantly with contacting the sample with the set of binding agents. Preferably, the treatment exposes a binding site of the binding agent on the Gram-positive bacterial antigen or on the Gram-negative bacterial antigen. Methods for treating the sample to expose a binding site for the binding agent on either the Gram-positive bacterial antigen or Gram-negative bacterial antigen are as described for the first aspect of the invention.

In certain embodiments, the donor blood or blood product determined to have an absence of a clinically relevant amount of Gram-positive bacteria according to the method of the second aspect of the invention is transferred to a recipient mammal In certain embodiments, the donor blood or blood product determined to have an absence of a clinically relevant amount of Gram-negative bacteria according to the method of the third aspect of the invention is transferred to a recipient mammal. Preferably, the donor mammal and the recipient mammal are of the same species.

In certain preferred embodiments, the binding agents that specifically bind to a Gram-positive bacterial antigen comprise antibodies or antibody derivatives that specifically bind to a Gram-positive bacterial antigen. In certain embodiments, the binding agents that specifically bind to a Gram-positive bacterial antigen comprise an antibiotic, wherein the antibiotic is not vancomycin. Preferably, the binding agents that specifically bind to a Gram-positive bacterial antigen specifically bind to the lipotechoic acid structure of the Gram-positive bacteria In certain preferred embodiments, the binding agents that specifically bind to a Gram-negative bacterial antigen comprise antibodies or antibody derivatives that specifically bind to a Gram-negative bacterial antigen. In certain preferred embodiments, the binding agents that specifically bind to a Gram-negative bacterial antigen comprise a molecule selected from the group consisting of a Limulus antilipopolysaccharide factor (LALF), a lipopolysaccharide binding protein (LBP), a bactericidal/permeability-increasing protein (BPI), and an antibiotic, such as polymixin or bacitracin. Preferably, the binding agents that specifically bind to a Gram-negative bacterial antigen specifically bind to the lipopolysaccharide structure of the Gram-negative bacteria.

In a fourth aspect, the invention provides a kit for screening for the presence of a clinically relevant amount of bacteria in donor blood or a donor blood product from a donor mammal for transfer to a recipient mammal comprising a set of binding agents, wherein the set of binding agents comprises binding agents that specifically bind to Gram-negative bacterial antigen and binding agents that specifically bind to Gram-positive bacterial antigen, and a means for detecting binding of the set of binding agents to a sample of the donor blood or blood product, wherein binding indicates the presence of a clinically relevant amount of bacteria in the donor blood or blood product and no binding indicates the absence of a clinically relevant amount of bacteria in the donor blood or blood product In preferred embodiments, the donor and/or recipient mammal is a human or a domesticated mammal.

In accordance with the fourth aspects of the invention, the terms, "binding," "antigen," "blood or blood product," "Gram-negative bacteria," "Gram-positive bacteria," "clinically relevant amount," "specifically binds," and "binding agent" are defined above.

As used herein, by "means for detecting binding" is meant any method known in the art to detect binding of a binding agent to a target ligand (i.e., to a LPS or LTA structure antigen). Preferred means for detecting binding include the immunoassays described below. Various "means for detecting binding" are known to the ordinarily skilled biologist and include, without limitation, lateral flow assay, ELISA, RIA, FACScan analysis, Western blotting analysis, immunoprecipitation, agglutination assays, particle-based and separation and non-separation assays. Separation ("heterogeneous") assays are assays in which bound and free labeled species are separated. Non-separation ("homogeneous") assays are assays in which binding of the labeled species to the complimentary binder modulates a property of the label, and therefore bound and free components can be distinguished without using a separation step. Separation assays may be divided into two basic formats, competitive assays, in which analyte and labeled analyte compete for a limited number of binding sites, and sandwich ("extraction") assays in which a reagent in excess extracts analyte from a sample. Reagents and samples may be mixed simultaneously or sequentially depending on the protocol developed. To improve assay sensitivity, one component may be labeled with a substance that can amplify the signal to detect a small number of binding events, this may include; radioisotopes, fluorescent dyes, enzymes, chemiluminescent compounds, metal atoms, metal sols or compounds, stable free radicals, viruses or bacteriophages, cofactors, latex particles substrates, erythrocytes, antibodies, inhibitors, apoenzymes, electroactive substances, fogging agents, spectral sensitizers, colored dyes, phosphorescent dyes, liposomes and electrophores.

It will be understood that any of these means for detecting binding may employ automation to perform and/or analyze the results of the assay.

In certain embodiments of the fourth aspect of the invention, the kit further comprises means for treating the sample, wherein the treatment exposes a binding site for the binding agent on the Gram-negative bacterial antigen or on the Gram-positive bacterial antigen.

By "means for treating" is meant any method or treatment that exposes a binding site of the binding agent on the Gram-negative bacterial antigen or on the Gram-positive bacterial antigen thereof. Such means include, without limitation, physical manipulation, including homogenization (with, for example, a Dounce homogenizer), sonication, and boiling. Other "means for treating" include treatment of the sample with chemical solutions or compounds including, without limitation, detergents (e.g., SDS or octoxynol, which is sold under the trademark Triton®), alkaline lysis solutions (e.g., a basic solution), acidic lysis solutions (e.g., an acidic solution), EDTA, EGTA, surfactants, metal ions, cations, anions, chelators, and enzymes.

In one embodiment of the fourth aspect of the invention, the donor blood or blood product determined to have an absence of a clinically relevant amount of bacteria is transferred to a recipient mammal, wherein the donor mammal from which the sample of blood or blood product was obtained and the recipient mammal are of the same species. Preferably, a kit of the invention is kept at the location (e.g., hospital) where the recipient patient will be administered the transfusion of donor blood or blood product. Using a kit of the invention, the attending health care professional can quickly determine if the donor blood is free of a clinically relevant amount of a contaminating bacteria. Once such a determination is made, and the blood or blood product is found to be free of a clinically relevant amount of bacteria contamination, the blood or blood product may be transfused to the recipient patient.

In preferred embodiments of the fourth aspect of the invention, the binding agents that specifically bind to a Gram-negative bacterial antigen comprise antibodies or antibody derivatives that specifically bind to a Gram-negative bacterial antigen. In certain preferred embodiments, the binding agents that specifically bind to a Gram-negative bacterial antigen comprise a molecule selected from the group consisting of a Limulus antilipopolysaccharide factor (LALF), a lipopolysaccharide binding protein (LBP), a bactericidal/permeability-increasing protein (BPI), and an antibiotic, such as polymixin or bacitracin. Preferably, the binding agents that specifically bind to a Gram-negative bacterial antigen specifically bind to the lipopolysaccharide structure of the Gram-negative bacteria. In a certain preferred embodiment, the binding agents that specifically bind to a Gram-positive bacterial antigen thereof comprise antibodies or antibody derivatives that specifically bind to a Gram-positive bacterial antigen. In certain embodiments, the binding agents that specifically bind to a Gram-positive bacterial antigen comprise an antibiotic, wherein the antibiotic is not vancomycin. Preferably, the binding agents that specifically bind to a Gram-positive bacterial antigen specifically bind to the lipotechoic acid structure of the Gram-positive bacteria.

In various embodiments of the fourth aspect of the invention, the binding agents that specifically bind to a Gram-negative bacterial antigen are detectably labeled with a first reporter molecule and the binding agents that specifically bind to a Gram-positive bacterial antigen are detectably labeled with a second reporter molecule. In one embodiment, the first reporter molecule and the second reporter molecule are the same. In another embodiment, the first reporter molecule and the second reporter molecule are not the same. Preferably, one or both of the first reporter molecule and the second reporter molecule is a molecule with enzymatic activity, a particle (e.g., a gold sol particle or a latex particle), a radio-labeled molecule, a fusion molecule, a fluorogenic molecule, a chromatic molecule, or a molecule that is specifically bound by a secondary binding agent. Such detectably labeled binding agents of the kit of the invention as are described above. It will be understood that where the reporter molecule detectably labeled to the binding agent is a molecule with enzymatic activity, the substrate for the enzyme is also included in the kit of the invention.

In a preferred embodiment of the fourth aspect of the invention, the set of binding agents is immobilized on a solid-phase support (e.g., a micro-titer plate).

In a fifth aspect, the invention provides a kit for screening for the presence of a clinically relevant amount of Gram-positive bacteria in donor blood or a donor blood product from a donor mammal for transfer to a recipient mammal comprising a set of binding agents, wherein the set of binding agents comprises binding agents that specifically bind to a Gram-positive bacterial antigen, and a means for detecting binding of the set of binding agents to a sample of the donor blood or blood product, wherein binding indicates the presence of a clinically relevant amount of Gram-positive bacteria in the donor blood or blood product and no binding indicates the absence of a clinically relevant amount of Gram-positive bacteria in the donor blood or blood product. Preferably, the donor and/or recipient mammal is a human or a domesticated mammal.

In a sixth aspect, the invention provides a kit for screening for the presence of a clinically relevant amount of Gram-negative bacteria in donor blood or a donor blood product from a donor mammal for transfer to a recipient mammal comprising a set of binding agents, wherein the set of binding agents comprises binding agents that specifically bind to a Gram-negative bacterial antigen, and a means for detecting binding of the set of binding agents to a sample of the donor blood or blood product, wherein binding indicates the presence of a clinically relevant amount of Gram-negative bacteria in the donor blood or blood product and no binding indicates the absence of a clinically relevant amount of Gram-negative bacteria in the donor blood or blood product. Preferably, the donor and/or recipient mammal is a human or a domesticated mammal.

In accordance with the fifth and sixth aspects of the invention, the terms, "means for binding," "binding," "antigen," "blood or blood product," "Gram-negative bacteria," "Gram-positive bacteria," "clinically relevant amount," "specifically binds," and "binding agent" are defined above.

In preferred embodiments of the fifth and sixth aspects of the invention, the kit further comprises means for treating the sample, wherein the treatment exposes a binding site for the binding agent on the Gram-negative bacterial antigen or on the Gram-positive bacterial antigen. "Means for treating" is as defined in the fourth aspect of the invention.

Any of the kits of the fourth, fifth, and sixth, aspects of the invention may be employed at the same time as ABO matching, Rh matching, and/or MHC matching of the donor blood or blood product and the intended recipient. Preferably, the clinically relevant amount of bacteria-free donor blood or blood product is administered as a transfusion to the patient not more than 42 days following the initiation of testing, more preferably, not more than 30 days post-testing, more preferably, not more than 2 weeks post-testing, more preferably, not more than 7 days post-testing, still more preferably, not more than 3 days post testing, even more preferably, not more than 2 days post testing, even more preferably, not more than 24 hours post-testing, even more preferably, not more than 12 hours post-testing, even more preferably, not more than 6 hours post-testing, and most preferably, the donor blood or blood product found to lack a clinically relevant amount of bacteria is transfused into the recipient within 3 hours of the initiation of testing. Most preferably, the blood or blood product is whole blood, hematopoietic stem cells, leukocytes, platelets, red blood cells, plasma, or serum.

The invention also provides methods and kits for screening for the presence of any contamination bacteria in a donor tissue or organ prior to transplanting the donor tissue or organ into the recipient mammal, which is preferably of the same species as the donor species. Donor tissues and organs are routinely stored, albeit briefly, in a fluid, such as physiological saline solution or a nutrient storage buffer. The presence of bacteria in the storage fluid indicates the presence of contaminating bacteria in the tissue. Such contaminating bacteria may accelerate rejection of the transplanted tissue or organ by the recipient mammal. Accordingly, in a seventh aspect, the invention provides a method for screening for the presence of a clinically relevant amount of bacteria in a tissue from a mammal wherein the tissue is stored in a fluid, comprising contacting a sample of the fluid with a set of binding agents, wherein the set of binding agents comprises binding agents that specifically bind to a Gram-negative bacterial antigen and binding agents that specifically bind to a Gram-positive bacterial antigen, and determining binding of the set of binding agents to the sample, wherein binding indicates the presence of a clinically relevant amount of bacteria in the tissue and no binding indicates the absence of a clinically relevant amount of bacteria in the tissue. Preferably, the donor and/or recipient mammal is a human or a domesticated mammal.

In accordance with the seventh aspect of the invention, the terms, "binding," "antigen," "Gram-negative bacteria," "Gram-positive bacteria," "clinically relevant amount," "specifically binds," and "binding agent" are defined above.

The term, "tissue," means any tissue or organ of the body. Examples of tissues of the invention include, without limitation, the kidney, liver, heart, skin, bone marrow, spleen, thymus, pancreas, intestines, and neurological tissue.

In certain embodiments of the seventh aspect of the invention, the sample is treated prior to or concomitantly with contacting the sample with the set of binding agents. In certain embodiments, the treatment exposes a binding site of the binding agent on the Gram-negative bacterial antigen or on the Gram-positive bacterial antigen. Methods of treatment that expose a binding site on the binding agent on a Gram-negative bacterial antigen or on a Gram-positive bacterial antigen are as described for the first aspect of the invention. In certain embodiments of the seventh aspect of the invention, the donor tissue determined to have an absence of a clinically relevant amount of bacteria is transferred to a recipient mammal Preferably, the donor mammal from which the tissue was obtained and the recipient mammal are of the same species. In certain preferred embodiments, the binding agents that specifically bind to a Gram-negative bacterial antigen comprise antibodies or antibody derivatives that specifically bind to a Gram-negative bacterial antigen. In certain preferred embodiments, the binding agents that specifically bind to a Gram-negative bacterial antigen comprise a molecule selected from the group consisting of a Limulus anti-lipopolysaccharide factor (LALF), a lipopolysaccharide binding protein (LBP), a bactericidal/permeability-increasing protein (BPI), and an antibiotic, such as polymixin or bacitracin. Preferably, the binding agents that specifically bind to a Gram-negative bacterial antigen specifically bind to the lipopolysaccharide structure of the Gram-negative bacteria. In certain preferred embodiments, the binding agents that specifically bind to Gram-positive bacteria or an antigen thereof comprise antibodies or antibody derivatives that specifically bind to Gram-positive bacteria or an antigen thereof. In certain embodiments, the binding agents that specifically bind to Gram-positive bacteria or an antigen thereof comprise an antibiotic, wherein the antibiotic is not vancomycin. Preferably, the binding agents that specifically bind to a Gram-positive bacterial antigen specifically bind to the lipotechoic acid structure of the Gram-positive bacteria In various embodiments of the seventh aspect of the invention, the binding agents that specifically bind to a Gram-negative bacterial antigen are detectably labeled with a first reporter molecule and the binding agents that specifically bind to a Gram-positive bacterial antigen thereof are detectably labeled with a second reporter molecule. In certain embodiments, the first reporter molecule and the second reporter molecule are the same. In another embodiment, the first reporter molecule and the second reporter molecule are not the same. Preferably, one or both of the first reporter molecule and the second reporter molecule is a molecule with enzymatic activity, a radio-labeled molecule, a fusion molecule, a fluorogenic molecule, a metal sol, a particle, a chromatic molecule, or a molecule that is specifically bound by a secondary binding agent.

In certain preferred embodiments of the seventh aspect of the invention, the set of binding agents is immobilized on a solid-phase support (e.g., a micro-titer plate).

In an eighth aspect, the invention provides a method for screening for the presence of a clinically relevant amount of Gram-positive bacteria in a donor tissue from a donor mammal for transfer to a recipient mammal, wherein the donor tissue is stored in a fluid, comprising contacting a sample of fluid with a set of binding agents, wherein the set of binding agents comprises binding agents that specifically bind to a Gram-positive bacterial antigen, and determining binding of the set of binding agents to the sample, wherein binding indicates the presence of a clinically relevant amount of Gram-positive bacteria in the donor tissue and no binding indicates the absence of a clinically relevant amount of Gram-positive bacteria in the donor tissue. Preferably, the donor and/or recipient mammal is a human or a domesticated mammal.

In a ninth aspect, the invention provides a method for screening for the presence of a clinically relevant amount of Gram-negative bacteria in a donor tissue from a donor mammal for transfer to a recipient mammal, wherein the donor tissue is stored in a fluid, comprising contacting a sample of the fluid with a set of binding agents, wherein the set of binding agents comprises binding agents that specifically bind to a Gram-negative bacterial antigen, and determining binding of the set of binding agents to the sample, wherein binding indicates the presence of a clinically relevant amount of Gram-negative bacteria in the donor tissue and no binding indicates the absence of a clinically relevant amount of Gram-negative bacteria in the donor tissue. Preferably, the donor and/or recipient mammal is a human or a domesticated mammal.

In accordance with the eighth and ninth aspects of the invention, the terms, "binding," "antigen," "tissue," "Gram-negative bacteria," "Gram-positive bacteria," "clinically relevant amount," "specifically binds," and "binding agent" are defined above. Preferably, any of the methods of the seventh, eighth, and ninth aspects of the invention is performed when the tissue is tested for ABO match, Rh match, and/or MHC match between with the intended recipient.

In certain embodiments of the eighth and ninth aspects of the invention, the sample is treated prior to or concomitantly with contacting the sample with the set of binding agents. Methods for treating the sample to expose a binding site for the binding agent on either the Gram-positive bacterial antigen or the Gram-negative bacterial antigen are as described for e first aspect of the invention.

In certain embodiments of the eighth and ninth aspects of the invention, the donor tissue determined to have an absence of a clinically relevant amount of Gram-positive bacteria or absence of a clinically relevant amount of Gram-negative bacteria is transferred to a recipient mammal. Preferably, the donor mammal from which the tissue was obtained and the recipient mammal are of the same species.

In a tenth aspect, the invention provides a kit for screening for the presence of a clinically relevant amount of bacteria in a donor tissue from a donor mammal for transfer to a recipient mammal wherein the tissue is stored in a fluid, comprising a set of binding agents, wherein the set of binding agents comprises binding agents that specifically bind to a Gram-negative bacterial antigen and binding agents that specifically bind to a Gram-positive bacterial antigen, and a means for detecting binding of the set of binding agents to a sample of the fluid, wherein binding indicates the presence of a clinically relevant amount of bacteria in the donor tissue and no binding indicates the absence of a clinically relevant amount of bacteria in the donor tissue. Preferably, the donor and/or recipient mammal is a human or a domesticated mammal.

In an eleventh aspect, the invention provides a kit for screening for the presence of a clinically relevant amount of Gram-positive bacteria in a donor tissue from a donor mammal for transfer to a recipient mammal, wherein the donor tissue is stored in a fluid, comprising a set of binding agents, wherein the set of binding agents comprises binding agents that specifically bind to a Gram-positive bacterial antigen, and a means for detecting binding of the set of binding agents to a sample of the fluid, wherein binding indicates the presence of a clinically relevant amount of Gram-positive bacteria in the donor tissue and no binding indicates the absence of a clinically relevant amount of Gram-positive bacteria in the donor tissue. Preferably, the donor and/or recipient mammal is a human or a domesticated mammal.

In a twelfth aspect, the invention provides a kit for screening for the presence of a clinically relevant amount of Gram-negative bacteria in a donor tissue from a donor mammal for transfer to a recipient mammal wherein the donor tissue is stored in a fluid, comprising a set of binding agents, wherein the set of binding agents comprises binding agents that specifically bind to a Gram-negative bacterial antigen, and a means for detecting binding of the set of binding agents to a sample of the fluid, wherein binding indicates the presence of a clinically relevant amount of Gram-negative bacteria in the donor tissue and no binding indicates the absence of a clinically relevant amount of Gram-negative bacteria in the donor tissue. Preferably, the donor and/or recipient mammal is a human or a domesticated mammal.

In accordance with the tenth, eleventh, and twelfth aspects of the invention, the terms, "means for binding," "binding," "antigen," "tissue," "Gram-negative bacteria," "Gram-positive bacteria," "clinically relevant amount," "specifically binds," and "binding agent" are defined above. In preferred embodiments of the eleventh and twelfth aspects of the invention, the kit further comprises means for treating the sample, wherein the treatment exposes a binding site of the binding agent on the Gram-negative bacterial antigen or on the Gram-positive bacterial antigen.

In certain embodiments of the tenth, eleventh, and twelfth aspects of the invention, the kit further comprises a means for treating the sample, wherein the treatment exposes a binding site for the binding agent on the Gram-negative bacterial antigen or on the Gram-positive bacterial antigen. Means for treating the sample are as described for the fourth aspect of the invention. In various embodiments, the donor tissue determined to have an absence of a clinically relevant amount of bacteria is transferred to a recipient mammal. Preferably, the donor mammal from which the tissue was obtained and the recipient mammal are of the same species.

Preferably, a kit of the invention is kept at the location (e.g., hospital) where the recipient patient will be administered the donor tissue via, for example, a transplantation or a transfusion. Using a kit of the invention, the attending health care professional can quickly determine if the donor tissue is free of a clinically relevant amount of a contaminating bacteria Once such a determination is made, and the donor tissue is found to be free of a clinically relevant amount of bacterial contamination, the donor tissue is transplanted into the recipient patient.

Any of the kits of the tenth, eleventh, and twelfth aspects of the invention may be employed at the same time as ABO matching, Rh matching, and/or MHC matching of the donor tissue and the intended recipient. Preferably, the tissue is screening using the methods and kits of the seventh, eighth, ninth, tenth, eleventh, and twelfth aspects of the invention a relatively short time prior to transplanting the tissue. Preferably, the donor tissue is transplanted into the patient not more than 42 days following the initiation of testing, more preferably, not more than 30 days post-testing, more preferably, not more than 2 weeks post-testing, more preferably, not more than 7 days post-testing, still more preferably, not more than 3 days post testing, even more preferably, not more than 2 days post testing, even more preferably, not more than 24 hours post-testing, even more preferably, not more than 12 hours post-testing, even more preferably, not more than 6 hours post-testing, and most preferably, the donor tissue found to lack a clinically relevant amount of bacteria is transplanted into the recipient within 3 hours of the initiation of testing.

Although not exhaustive, a number of potential immunoassay formats are described in the following examples which, when used in conjunction with a LTA or LPS specific binding agent, can generate a pan-generic assay for class microbial detection. Thus, the following Fat examples are intended to further illustrate certain particularly preferred embodiments of the invention and are not intended to limit the scope of the invention.

EXAMPLE I

A bacterial detection method of the invention can follow a conventional particle-based immunoassay format. In this approach, binding agents that specifically bind to an antigenic region on the bacterial cell wall can be utilized as immunological targets and can form the basis for detecting the bacteria in the blood products. A schematic of the device used in this example is shown on FIGS. 3A–3D. In one embodiment, the binding agents that specifically bind to Gram-positive bacteria, Gram-negative bacteria, or both, are pooled together, and then roughly divided, such that the two populations of binding agents each comprises a mixture of binding agents. One population is bound to the membrane at the base of the device shown in FIGS. 3A–3D. The second population is used to coat brightly dyed latex particles (i.e., the latex particles coated with the binding agent have been impregnated with a dye so that they are intensely colored).

In another embodiment, the same binding agent (i.e., all binding agent molecules specifically recognize the same antigenic epitope) is divided into two populations. Again, one population is bound to the membrane at the base of the device of FIGS. 3A–3D, while the second population is used to coat brightly dyed latex particles. The same binding agent (i.e., molecules that specifically bind to the same epitope) could be utilized, since multiple recognition sites are present on the bacterial surface.

The binding agent-coated beads are placed into the device, such that they do not bind the membrane.

To use the device shown on FIGS. 3A–3D to detect the presence of a clinically relevant amount of bacteria in a blood or blood product, the following steps are performed. First, a sample is extracted under sterile conditions from donor blood or a donor blood product. Alternatively, a sample may be extracted from the fluid in which a donor organ or tissue is being stored (e.g., the nutrient storage fluid in which a donor kidney is stored).

Next, an appropriate volume of the sample is applied to the test device, as shown on FIGS. 3A–3D. The sample may be tested straight (i.e., undiluted or untreated), or it may have been diluted with a buffering/extraction reagent, or it may be treated by physical or chemical means, whereby the treatment exposes a binding site of the binding agent on bacteria (or antigen thereof) present in the sample. For example, the treatment may result in the disruption of the bacterial cell wall. In another example, the treatment may result in an antigen being cleaved off the cell wall, and thereby exposing a binding site on the antigen.

The sample travels a predestined path in the device due to the wicking action of an absorbent membrane. The bacteria present in the sample binds to the binding agent-labeled latex particles.

The sample mixes with the binding agent-labeled latex particles and migrates along the absorbent wick to a pre-defined region where anti-bacteria antibodies have been immobilized. The immobilized binding agents capture the bacteria-anti-bacteria coated dyed latex bead complexes, and a colored spot forms indicating a positive result.

EXAMPLE II

In another embodiment of the method described in Example I, the latex-bound binding agents are binding agents that specifically recognize either Gram-negative bacteria or Gram-positive bacteria, or both. However, each of these anti-bacteria binding agents has an epitope that is common to all binding agents. In this example, all of the anti-bacteria binding agents are murine antibodies. The membrane bound binding agents do not specifically bind bacteria; rather, they specifically bind the murine determinants on the constant region of the murine anti-bacteria antibodies. These anti-mouse binding agents are called secondary binding agents, because they do not specifically bind the bacteria, but rather, specifically bind the binding agent that is specifically bound to the bacteria.

EXAMPLE III

An agglutination assay is yet another method to detect clinically relevant amounts of bacteria in blood, a blood product, or fluid from a donor tissue. In this example of an agglutination assay, latex particles coated with binding agents that specifically bind to bacterial species are employed. These latex particles agglutinate in the presence of clinically relevant amounts of bacterial species. A positive reaction is indicated by the development of an agglutinated pattern. In a negative reaction the latex does not agglutinate and the milky appearance remains substantially unchanged.

In this method, a test device such as that shown on FIGS. 4A–4D is employed. A sample extracted under sterile conditions from a donor blood or blood product is applied to the test device. Alternatively, a sample extracted from a fluid in which a donor organ or tissue is stored may be applied to the test device. The sample may be tested straight (i.e., undiluted or untreated), diluted with a buffering/extraction reagent, or treated such that the treatment exposes a binding site of the binding agent on any bacteria (or antigen thereof) present in the sample. Next, latex beads coated with binding agents that specifically bind to bacteria are added to the biological sample in the text device. The contents are mixed to ensure component homogeneity.

Bacteria in the biological samples will specifically bind to the anti-bacteria antibodies on the latex beads. As a result of the multiple antigenic sites on the bacterial surface, antibody coated latex particles form a bridge between adjacent bacterial cells In the presence of clinically relevant amounts of bacterial cells in the biological sample a crossed-linked matrix is formed. Beyond the pre-defined clinically relevant amount of bacteria in the sample (as defined above), the matrix grows to the point of becoming visible as an "agglutination" pattern in the test well. After a predetermined time to allow the growth of such a matrix the results are visually read, the presence of bacterial antigen results in the formation of the characteristic pattern shown in FIG. 4D.

EXAMPLE IV

Yet another method to detecting the presence of a clinically relevant amount of bacteria in a blood or blood product employs a standard Enzyme Linked Immunosorbant Assays (ELISA) format. Microtiter (ie., 96 well) plate ELISA formats utilize multiple discrete reaction wells, each representing a unique test environment. Microtiter plate formats allow for a higher throughput testing capability, the application of automated sample handing, reagent addition, reaction detection, and quantitative results interpretation. The development of microtiter plate ELISAs is well known and practiced. For the detection of large molecular weight species with multiple binding sites, as with bacterial surface antigens, a sandwich immunoassay format is a preferred format. Sandwich immunoassays are constructed by passively or covalently placing a binding agent that specifically binds to either Gram-negative or Gram-positive bacteria (or both) on the polystyrene (or other materials) surface of the microtiter plate well, such that the binding agent adheres to the surface of the microtiter plate well. The immunological detection proceeds as follows.

First, a sample is extracted under sterile conditions from either a donor blood or a donor blood product, or from the fluid in which is stored a donor organ or tissue. The sample may be diluted or undiluted, or treated such that the treatment exposes a binding site of the binding agent on any bacteria (or antigen thereof) present in the sample. An appropriate volume of the sample is applied to the test well. Bacteria present in the biological sample will specifically complex with the surface bound anti-bacteria binding agents on the surface of the microtiter plate well The well is next aspired (or dumped) to remove unbound sample in the well. A specifically formulated wash solution is added to the well to wash non-specifically bound bacteria (and other sample constituents) from the surface of the microtiter plate well.

Next, a solution containing a binding agent detectably labeled with a reporter molecule is added to the reaction well. The detectably labeled binding agent in this solution specifically binds to an antigen that defines the type of bacteria present in the biological sample, and may be different or the same as the surface-bound binding agent. The detectably labeled binding agent is chemically coupled to a reporter molecule (a reporter molecule with enzymatic activity, in the specific case of an ELISA) which is used to indicate the absence or presence of bacteria in the sample. It should be noted that the reporter molecule can be created from a variety of species, and is selected to minimize interference with the antibody binding reaction. Enzymes are utilized predominantly in Enzyme Linked Immunosorbant Assays (ELISA), but other reporter molecules may also be employed, including, without limitation, chromophores, fluorophores, radioisotopes, chemiluminescent compounds, electrochemically active compounds, metals, particles, magnetic species and secondary labels such as biotinfavidin or other similar species. The detectably labeled binding agent that results from the chemical coupling of the specific binding agent with the reporter molecule is allowed to complex with the anti-bacteria binding agent/bacteria complex forming an anti-bacteria binding agent/bacteria/anti-bacteria detectably labeled binding agent "sandwich".

After an appropriate time period, the detectably labeled binding agent solution is removed from the well. The well may then be washed with a specifically formulated wash solution to separate the bound conjugate from the unbound conjugate in the microtiter plate well.

The specifically bound detectably labeled binding agent in the microtiter plate well can be detected by appropriate means. This includes direct measurement in the case of fluorophores, chromophores, chemiluminescent, electroactive and indirect measurement in the case of labels such as enzymes. The number of specifically bound detectably labeled binding agents is directly proportional to the amount of bacteria present in the biological sample. This proportionality is the basis of a quantitation methodology that can be utilized to specifically determine the amount of bacteria present in the sample. A standard response curve can be established by measuring the response of specifically bound detectably labeled binding agent as a function of known quantities of bacteria present in calibrant samples. Interpolation of results from the standard response curve describes the concentration of bacteria in the unknown biological sample.

EXAMPLE V

An additional method for screening for the presence of a clinically relevant amount of bacteria in blood, blood product, or the fluid in which a donor tissue is stored employs a competitive immunoassay format. Indeed, for the detection of small molecular weight species with single binding sites, such as the secreted lipopolysaccharide structures from the Gram-negative bacteria, a competitive immunoassay format is a preferred format. Competitive immunoassays are constructed by passively or covalently placing a binding agent that specifically binds to the secreted LPS structure (such as binding to the Lipid A portion of the LPS structure) on the polystyrene (or other material) surface of the microtiter plate well, such that the binding agent adheres to the surface of the microtiter plate well.

In one example of this competitive immunoassay format to detect the presence of a clinically relevant amount of Gram-negative bacteria, the immunological detection proceeds as follows. First, a sample is extracted under sterile conditions from the donor blood or blood product or from the fluid in which a donor organ or tissue is stored. The sample may be diluted or undiluted, or treated such that a binding site of a binding agent on the Gram-negative bacteria (or antigen thereof) is exposed, such as a binding site on the Lipid A component of the LPS. An appropriate volume of the sample is applied to the test well, which contains a binding agent that specifically binds to LPS. An appropriate volume of a solution containing a detectably labeled LPS molecule is simultaneously or sequentially added to the test well. The detectably labeled LPS molecule in this solution specifically binds to the binding agent in the test well The detectably labeled LPS molecule is chemically coupled to a reporter molecule (such as a reporter molecule with enzyme activity, in the specific case of an ELISA) which is used to indicate the presence or absence of bacteria in a sample. It should be noted that the reporter molecule can be created from a variety of species, and is selected to minimize interference with the antibody binding reaction. Enzymes are used predominantly in Enzyme Linked Immunosorbant Assays (ELISA), but other reporter molecules may also be employed, including, without limitation, chromophores, fluorophores, radioisotopes, chemiluminescent compounds, electrochemically active compounds, metals, particles, magnetic species and secondary labels such as biotin/avidin or other similar species. The detectably labeled LPS molecule is allowed to complex with the immobilized binding agent in the presence of the cell wall derived LPS, establishing a binding equilibrium. Preferably, the test well is a well on a microtiter plate.

After an appropriate time period, the detectably labeled LPS molecule/contaminating bacterial cell-derived LPS solution is removed from the test well. The well may be washed with a specifically formulated wash solution to separate bound conjugate from unbound conjugate in the microtiter well. The binding equilibrium established in the test well is a function of the concentration of cell derived LPS. In the absence of any contaminating clinically relevant amount of Gram-negative bacteria in the sample, and hence no bacterial cell-derived LPS, the detectably labeled LPS molecule is complexed to the surface bound binding agent. At elevated levels of bacteria, and hence elevated levels of contaminating bacterial cell-derived LPS, binding to the surface bound binding agent is partitioned between the two LPS species based on concentration. At low levels of contaminating bacterial cell-derived LPS, the majority of the binding agent binding sites are complexed with detectably labeled LPS molecule and an increased level of reporter signal is observed. At high levels of bacterial cell-derived LPS, the majority of the binding agent binding sites are complexed with bacterial cell-derived LPS and a decreased level of reporter signal is observed. Thus, the number of specifically bound detectably labeled LPS molecules is inversely proportional to the amount of contaminating Gram-negative bacteria present in the biological sample. A standard response curve can be established by measuring the response of the detectably labeled LPS molecule as a function of known quantities of bacteria present in calibrant samples. Interpolation of results from the standard response curve describes the concentration of Gram-negative bacteria in the unknown biological sample.

EXAMPLE VI

Yet another method for detecting the presence of a clinically relevant amount of bacteria in a blood or blood product employs a homogeneous immunoassay format. Homogeneous immunoassays are characterized by the ability of the bound and free components of the binder-ligand complexation reaction to be measured simultaneously. The properties of the label are modified upon binding of the complementary reactant such that separation of bound from unbound is not needed.

First, a sample is extracted under sterile conditions from the donor blood or blood product, or from a fluid in which is stored a donor tissue or organ. An appropriate volume of the test sample is mixed with a pre-treatment reagent such that small fragments of the cell wall structure are created. Such reagent may include (but not limited to) surfactants, chelators and enzymes to degrade the native antigenic structure to smaller molecular weight sub-components. Additionally, mechanical fragmentation (such as sonication) or kinetic energy (such as boiling) may be utilized to break down the cell wall into its sub-components. In this example, the treatment exposes a binding site of the binding agent on the Gram-negative bacteria or antigen thereof by resulting in the removal and degradation of the lipopolysaccharide structure in Gram-negative bacteria to its Lipid A or core units.

A sample of the degraded cell wall fragments is mixed with a reagent containing Lipid A (or core) antigen which has been chemically coupled with a fluorescent label. A known amount of anti-Lipid A (or anti-core) binding agent is added to the reaction mixture. Antigens that are bound to the binding agent will show a decreased level of molecular rotation whereas those not bound will show a relatively increased level of rotation. In a polarized light field, the polarized light will preferentially excite those molecules that are parallel to the plane of the incident light. The orientation of the emission species will determine the degree of polarization of the emitted light. If the molecular position of the emitting species is relatively stable, the fluorescence will be partially polarized. If instead of being fixed, the molecules are in a state of rapid oscillation, the molecular motion will decrease the degree of polarization. Fluorescent light emitted from the reactant mixture of cell wall fragment Lipid A (or core) antigen from any contaminating Gram-negative bacteria present in the sample, fluorescently labeled Lipid A (or core), and binding agent will show a high degree of light polarization at low cell wall fragment Lipid A (or core) levels (i.e., low levels of bacterial contamination in the sample) and a low degree of light polarization at high cell wall fragment Lipid A (or core) levels (ie., high levels of Gram-negative bacterial contamination in the sample), as compared to binding agent plus fluorescently labeled Lipid A (or core) without any sample. This response of differential levels of light polarization as a function of cell wall fragment Lipid A (or core) can be utilized as the basis of a binding assay to determine unknown concentrations of Lipid A (or core) and ultimately determine the presence or absence of Gram-negative bacteria in a sample.

Utilizing an antibody as a binding agent, the above detection technology is well known in the field as fluorescence polarization immunoassay, related techniques include fluorescence quenching immunoassay, time resolved fluoroimmunoassay, fluorescence enhanced immunoassay, fluorescence excitation transfer immunoassay and fluorophore release immunoassay. Alternatively, enzyme activity modulation as a function of binding agent complexation may also be used as an alternative homogeneous immunoassay format for detecting smaller fragments of bacterial cell wall constituents (and therefore determining the presence or absence of bacterial contamination). Each of these approaches is well documented and well known by those familiar with the art.

EXAMPLE VII

A modification of the method described in Example VI will screen for the presence of a clinically relevant amount of Gram-positive bacteria in a sample collected from donor blood, donor blood product, and/or the fluid in which a donor tissue is stored. In this example, a sample is extracted under sterile conditions from the donor blood, donor blood product, or fluid in which a donor tissue is stored. An appropriate volume of the test sample is mixed with a pre-treatment reagent such that small fragments of the cell wall structure are created. This treatment that results in the exposure of a binding site of a binding agent on the Gram-positive bacteria (or antigen thereof) may be treatment with a chemical, such as a surfactant, a chelator, and/or an enzyme to degrade the native antigenic structure to smaller molecular weight sub-components. The treatment may also be by mechanical means, using mechanical fragmentation (such as sonication) or kinetic energy (such as boiling) to break down the cell wall into its subcomponents thereby exposing a binding site of a binding agent on an antigenic component of the LTA structure. One specific example may be the isolation of the poly(glycerophosphate) chain from the lipoteichoic acid structures. Other structures of the Gram-positive cell wall can be easily anticipated by those knowledgeable in the field.

Next, a sample of the degraded cell wall fragments is mixed with reagent containing poly(glycerophosphate) antigen which has been chemically coupled with an enzyme label to form an enzyme conjugate. The enzyme conjugation is done in such a form that upon complexation with a binding agent the enzyme activity of the conjugate is modulated. Through either masking of the active site, or with conformational modifications to the enzyme, when a binding agent is complexed to the enzyme conjugate enzyme activity is reduced, without the binding agent complexed to the conjugate enzyme activity is restored. This enzyme activity modulation is the basis of a commonly utilized homogeneous assay format.

Next, a known amount of anti-poly(glycerophosphate) binding agent is added to a reaction mixture which contains fixed amounts of binding agent and enzyme conjugate. Additionally, a known volume of the blood (or blood product or tissue fluid) treated to degrade the bacterial cell wall constituents is added. If no bacteria are present in the blood, blood product, or fluid from a donor tissue sample, then the available binding sites on the binding agent will be complexed to the enzyme conjugate. The enzyme conjugate will show a reduced level of enzymatic activity in the bound state and minimal substrate conversion will occur. At high levels of cell wall derived antigen from a high level of contaminating Gram-positive bacteria present in the sample, the majority of binding sites on the binding agent will be occupied by native sell wall antigen (poly (glycerophosphate) as an example) thereby allowing the enzyme conjugate to exist in the non-complexed state. In this non-complexed state, the enzyme activity is restored and elevated levels of substrate turn-over are observed.

A slight modification to the procedure involves the utilization of enzyme fragments, one of which is labeled with an antigen fragment. In the presence of binding agent the enzyme fragment is unavailable to complex with the required additional fragment to create a whole functional enzyme. When binder is complexed with cell wall derived antigen from contaminating Gram-positive bacteria present in the sample, it is unavailable to complex with the enzyme fragments thereby allowing them to combine and form an active enzyme. Modifications to these approaches are well known and understood by those in the field as enzyme modulation binder assay formats.

EXAMPLE VIII

Modifications of the assays described in Examples IV, V, VI, and VII incorporate the utilization of automated analytical equipment for assay execution and results calculation. Automation enables the application of the technology in a more reproducible format thereby allowing for improved assay performance as well as reduced detection level of bacterial contamination. Numerous comprehensive immunoassay systems are commercially available and are used for routine immunodiagnostic testing in the hospitals central laboratory. Application of the above-described technology can be readily anticipated as being incorporated onto any of these automated systems. The use of alternative separation methodologies (solid phase, liquid phase, magnetic particles, electrical charge partitioning etc.) can also be anticipated within this disclosure. Analogously, alternative detection methodologies (such as chromogenic, fluorogenic, electrochemical, chemiluminescent or radiometric) can likewise be anticipated by anticipated modifications to the detection method of the detectably labeled binding agent systems as well as a corresponding change to the detection system of the automated immunoassay system.

EXAMPLE IX

The pan-genera specificity of two representative, non-limiting binding agents of the invention was evaluated by probing surface antigen structures on both Gram-positive and Gram-negative bacteria. The binding agent that specifically binds to a Gram-positive bacterial antigen, namely Lipoteichoic acid, was monoclonal antibody clone 96-110 ((IgG1) (described in Fisher et al., PCT Publication No. WO 98/57994). The binding agent that specifically binds to a Gram-negative bacterial antigen, namely lipid A, was monoclonal antibody clone 26-5 (IgG2b) (commercially available from Biodesign International, Saco, Me., catalog number C61212M).

Figure 5:
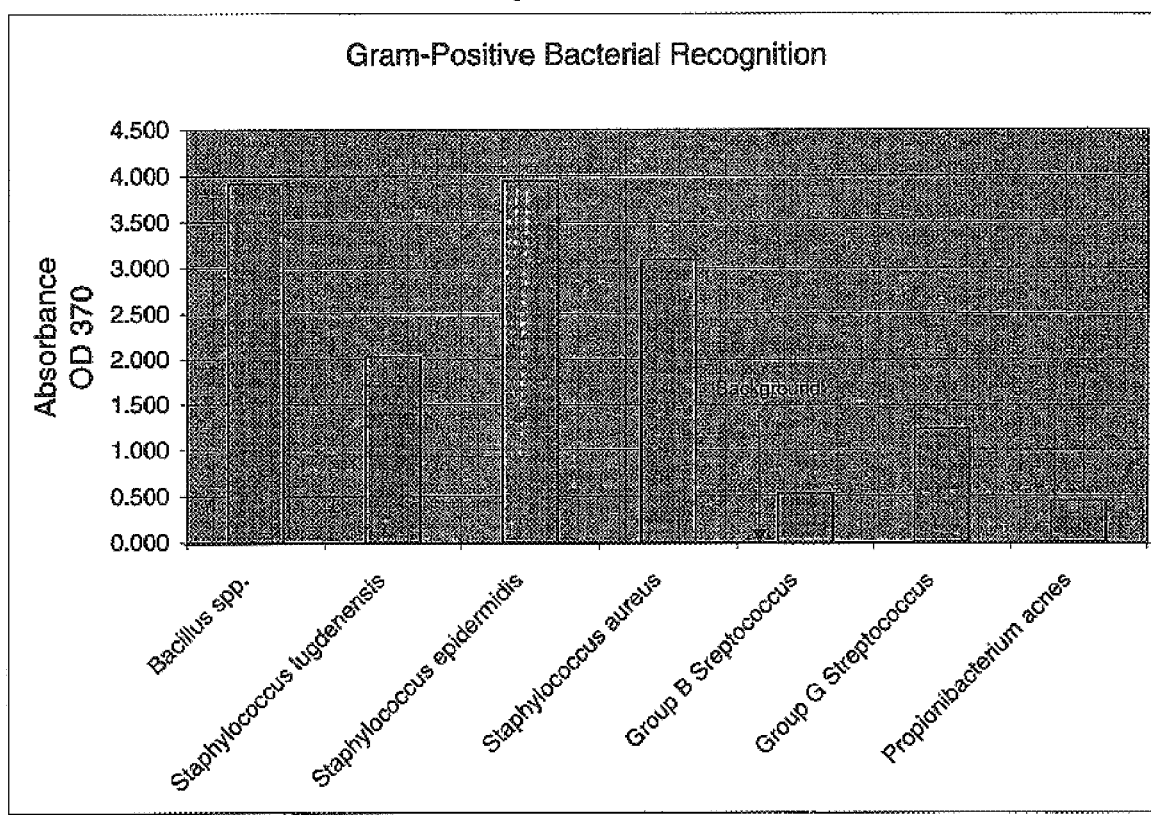
FIG. 5 is a graphical representation of the number of different (indicated) Gram-positive bacteria specifically bound by a non-limiting binding agent of the invention, anti-lipoteichoic acid antibody.
Figure 6:
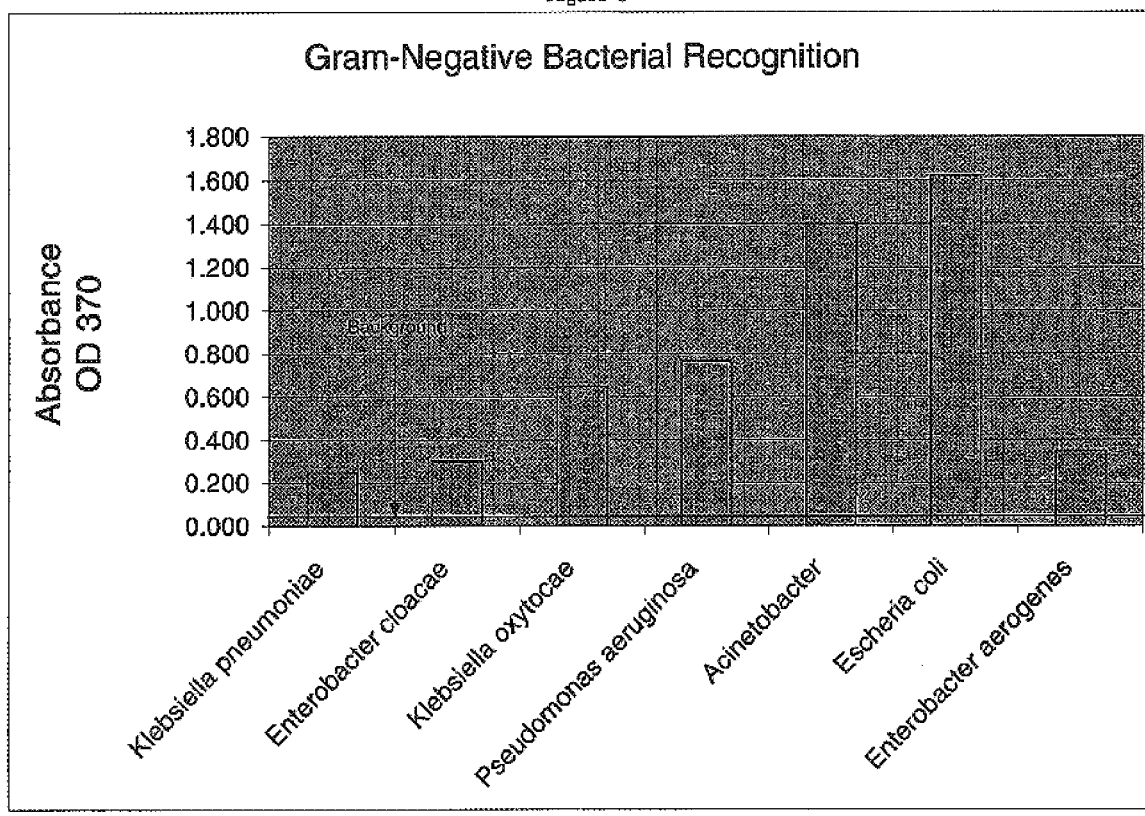
FIG. 6 is a graphical representation of the number of different (indicated) Gram-negative bacteria specifically bound by a non-limiting binding agent of the invention, anti-lipopolysaccharide antibody.

Fourteen bacteria were chosen for binding characterization: seven Gram-positive bacteria and seven Gram-negative (see FIGS. 5 and 6, respectively). These bacteria were chosen because they represent the bacterial species that have been identified during the three major national transfusion reaction studies (including the BaCon study in the United States, the Hemovigilance study in France and the SHOT study in the U.K).

To characterize the binding of Gram-positive and Gram-positive bacteria with the anti-lipotechoic acid monoclonal antibody and the anti-Lipid A monoclonal antibody, respectively, bacterial species from clinical isolates were streaked onto 5% Sheep blood agar plates (BBL) and grown overnight at 37° C. The resulting colonies were inoculated into Tryptic Soy Broth (30 mg/ml, Sigma) in PBS and rotated overnight at 37° C. Bacterial count was quantitated by turbidometric measurement at 620 nm. Whole cell bacteria were pelletized at 5000 rpm for fifteen minutes. The pelleted bacteria were resuspended in PBS to approximately $10^8$ colony forming units (CFU)/mL in phosphate buffered saline (PBS). 100 $\mu$L of bacterial suspension was added to each well of a single row of 96 well microtiter plates. This process was repeated for each of the seven Gram-Positive bacteria and each of the seven Gram-Negative bacteria. The plates were incubated one hour at 37° C. and then stored overnight at 4° C. The plates were then washed five times with 200 $\mu$L/well of 0.05% Tween-20 and stored dry at −20° C. until use.

To minimize non-specific binding, the bacteria-coated plates were blocked with 300 $\mu$L/well of 5% dry milk/0.05% Tween-20 in PBS. The plates were blocked overnight at room temperature and then washed 3x with PBS/Tween. The binding agents (ie., the anti-lipotechoic acid monoclonal antibody and the anti-Lipid A monoclonal antibody) were diluted to 5 $\mu$g/mL in PBS containing 4% BSA and 0.05% Tween-20. The solutions were mixed and filtered through 0.22 $\mu$m filters. 100 $\mu$L of solution was added to each well and the binding agents were allowed to react for one hour at 37° C. The plates were then washed 5 times with 0.05% Tween-20. A commercially available secondary antibody, Goat anti-mouse IgG (Heavy and light chains) HRP conjugate was diluted 1:5000 in PBS/1.5% BSA & 0.05% Tween-20. 200 $\mu$L of the secondary antibody solution was added to each well and the secondary antibody was allowed to bind for one hour at 37° C. The plates were subsequently washed once with PBS/0.05% Tween and three more times with PBS alone. To quantitate bacterial binding, 200 $\mu$L of Peroxidase TMB substrate (Sigma) was added to each well. Absorbance (OD 370 nm) was read in a kinetic format in the Dynax microtiter plate reader.

As shown in FIGS. 5 and 6, respectively, each of the seven Gram-positive and seven Gram-negative bacteria were specifically recognized by the anti-lipotechoic acid monoclonal antibody (Gram-positive; FIG. 5) and the anti-Lipid A monoclonal antibody (Gram-negative; FIG. 6), (Mean results from a triplicate measurement were plotted as a function of each of the recognized bacteria) As FIGS. 5 and 6 demonstrate, the extent of recognition varies between bacterial species but in all cases the bacteria are above background by at least two-fold. These data clearly indicate the feasibility of utilizing a common binding agent to recognize pan-generically both Gram-negative and Gram-positive bacteria. These bacteria are of specific interest since they represent the exact species of bacteria identified as causative agents in transfusion reactions.

What is claimed is:

1. A method for screening for the presence of a clinically relevant amount of bacteria in donor blood or blood product from a donor mammal for transfer into a recipient mammal, comprising: contacting a sample of the donor blood or blood product with a set of pan-generic antibodies, wherein the set of antibodies comprises antibodies that specifically bind to a Gram-negative bacterial antigen and antibodies that specifically bind to a Gram-positive bacterial antigen, detecting binding of the set of antibodies to the sample, wherein binding indicates the presence of a clinically relevant amount of bacteria in the donor blood or blood product and no binding indicates the absence of a clinically relevant amount of bacteria in the donor blood or blood product from the donor mammal, wherein the blood or blood product determined to have less than $1 \times 10^6$ colony forming units (CFU) per mL of bacteria is useful for transfer to the recipient mammal.

2. The method of claim 1, wherein the donor blood or blood product is selected from the group consisting of whole blood, leukocytes, hematopoietic stem cells, platelets, red blood cells, plasma, and serum.

3. The method of claim 1, wherein the antibodies that specifically bind to the Gram-negative bacterial antigen specifically bind to the lipopolysaccharide structure of the Gram-negative bacteria.

4. The method of claim 1, wherein the antibodies that specifically bind to the Gram-positive bacterial antigen specifically bind to the lipoteichoic acid structure of the Gram-positive bacteria.

5. The method of claim 1, wherein the set of antibodies is immobilized on a solid-phase support.

6. A method for screening for the presence of a clinically relevant amount of Gram-positive bacteria in donor blood product from a donor mammal for transfer into a recipient mammal, comprising: contacting a sample of the donor blood or blood product with a set of pan-generic antibodies, wherein the set of antibodies comprises antibodies that specifically bind to a Gram-positive bacterial antigen, detecting binding of the set of antibodies to the sample, wherein binding indicates the presence of a clinically relevant amount of Gram-positive bacteria in the donor blood or blood product and no binding indicates the absence of a clinically relevant amount of Gram-positive bacteria in the donor blood or blood product, and wherein the donor blood or blood product from the donor mammal determined to have less than $1 \times 10^6$ CFU per mL of Gram-positive bacteria is useful for transfer to the recipient mammal.

7. A method for screening for the presence of a clinically relevant amount of Gram-negative bacteria in donor blood product from a donor mammal for transfer to a recipient mammal, comprising: contacting a sample of the donor blood or blood product with a set of pan-generic antibodies, wherein the set of antibodies comprises antibodies that specifically bind to a Gram-negative bacterial antigen, detecting binding of the set of antibodies to the sample, wherein binding indicates the presence of a clinically relevant amount of Gram-negative bacteria in the donor blood or blood product and no binding indicates the absence of a clinically relevant amount of Gram-negative bacteria in the donor blood or blood product, and wherein the donor blood or blood product from the donor mammal determined to have less than $1 \times 10^6$ CFU per mL of Gram-negative bacteria is useful for transfer to the recipient mammal.

8. A method for screening for the presence of a clinically relevant amount of bacteria in a donor tissue from a donor mammal for transfer to a recipient mammal, wherein the donor tissue is stored in a fluid, comprising contacting a sample of the fluid with a set of pan-generic antibodies, wherein the set of antibodies comprises antibodies that specifically bind to a Gram-negative bacterial antigen and antibodies that specifically bind to a Gram-positive bacterial antigen, detecting binding of the set of antibodies to the sample, wherein binding indicates the presence of a clinically relevant amount of bacteria in the donor tissue and no binding indicates the absence of a clinically relevant amount of bacteria in the donor tissue, and wherein the donor tissue from the donor mammal determined to have less than $1 \times 10^6$ CFU per mL of bacteria is useful for transfer to the recipient mammal.

9. The method of claim 8, wherein the donor tissue determined to have an absence of a clinically relevant amount of bacteria is transferred to the second mammal.

10. The method of claim 8, wherein the donor tissue is selected from the group consisting of lung, heart, liver, skin, kidney, pancreas, spleen, and bone marrow.

11. A method for screening for the presence of a clinically relevant amount of Gram-positive bacteria in a donor tissue from a donor mammal for transfer to a recipient mammal, wherein the donor tissue is stored in a fluid, comprising contacting a sample of fluid with a set of pan-generic antibodies, wherein the set of antibodies comprises antibodies that specifically bind to a Gram-positive bacterial antigen, detecting binding of the set of antibodies to the sample, wherein binding indicates the presence of a clinically relevant amount of Gram-positive bacteria in the donor tissue and no binding indicates the absence of a clinically relevant amount of Gram-positive bacteria in the donor tissue, and wherein the donor tissue from the donor mammal determined to have less than $1 \times 10^6$ CFU per mL of Gram-positive bacteria is useful for transfer to the recipient mammal.

12. A method for screening for the presence of a clinically relevant amount of Gram-negative bacteria in a donor tissue from a donor mammal for transfer to a recipient mammal, wherein the donor tissue is stored in a fluid, comprising contacting a sample of the fluid with a set of pan-generic antibodies, wherein the set of antibodies comprises antibodies that specifically bind to a Gram-negative bacterial antigen, detecting binding of the set of antibodies to the Gram-negative bacterial antigen in the sample, wherein binding indicates the presence of a clinically relevant amount of Gram-negative bacteria in the donor tissue and no binding indicates the absence of a clinically relevant amount of Gram-negative bacteria in the donor tissue, and wherein the donor tissue from the donor mammal determined to have less than $1 \times 10^6$ CFU per mL of Gram-negative bacterial is useful for transfer to the recipient mammal.

13. The method of any of claims 1, 6, 7, 8, 11, and 12, wherein the set of antibodies are detectably labeled with a reporter molecule.

14. The method of claim 13, wherein said reporter molecule is selected from the group consisting of a molecule with enzymatic activity, a radio-labeled molecule, a fusion molecule, a fluorogenic molecule, a metal sol, a particle, a chromatic molecule, and a molecule that is specifically bound by a secondary agent.

15. The method of any of claims 1, 6, 7, 8, 11, and 12, wherein the clinically effective amount of bacteria is greater than $1 \times 10^5$ CFU/ml of blood, blood product, or tissue.

16. The method of any of claims 1, 6, 7, 8, 11, and 12, wherein the clinically effective amount of bacteria is greater than $1 \times 10^4$ CFU/ml of blood, blood product, or tissue.

17. The method of any of claims 1, 6, 7, 8, 11, and 12, wherein the clinically effective amount of bacteria is greater than $1 \times 10^3$ CFU/ml of blood, blood product, or tissue.

18. The method of claim 14, wherein the enzymatic molecule is selected from the group consisting of horseradish peroxidase, alkaline phosphatase, and β-galactosidase.

19. The method of claim 13, wherein said reporter molecule is bound to the binding agent by intermolecular association.

20. The method any of claims 1, 6, 7, 8, 11, and 12 further comprising the step of transferring the blood, blood product, or tissue to a recipient mammal.

* * * * *